United States Patent
Casellas et al.

(10) Patent No.: US 7,767,681 B2
(45) Date of Patent: Aug. 3, 2010

(54) 2-CARBAMIDE-4-PHENYLTHIAZOLE DERIVATIVES, PREPARATION THEREOF AND THERAPEUTIC USE THEREOF

(75) Inventors: Pierre Casellas, Montpellier (FR); Daniel Floutard, Combaillaux (FR); Pierre Fraisse, Juvignac (FR); Samir Jegham, Montferrier-sur-Lez (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 11/649,316

(22) Filed: Jan. 3, 2007

(65) Prior Publication Data

US 2007/0179126 A1 Aug. 2, 2007

Related U.S. Application Data

(63) Continuation of application No. PCT/FR2005/001729, filed on Jul. 5, 2005.

(30) Foreign Application Priority Data

Jul. 9, 2004 (FR) .................................. 04 07695

(51) Int. Cl.
  *A61K 31/497* (2006.01)
  *C07D 413/14* (2006.01)
(52) U.S. Cl. .................................. 514/254.02; 544/369
(58) Field of Classification Search ................. 544/369; 514/254.02
  See application file for complete search history.

(56) References Cited

U.S. PATENT DOCUMENTS

| | | | |
|---|---|---|---|
| 4,225,610 | A | 9/1980 | Tarayre et al. |
| 5,314,889 | A | 5/1994 | Boigegrain et al. |
| 6,506,751 | B1 | 1/2003 | Justus et al. |
| 7,504,511 | B2 | 3/2009 | Carayon |
| 2002/0115863 | A1 | 8/2002 | Patel et al. |
| 2002/0119962 | A1 | 8/2002 | Jacobs et al. |
| 2004/0048891 | A1 | 3/2004 | Kato et al. |
| 2006/0135575 | A1 | 6/2006 | Carayon |
| 2007/0259847 | A1 | 11/2007 | Casellas |

FOREIGN PATENT DOCUMENTS

| | | | |
|---|---|---|---|
| EP | 0 001 727 | | 5/1979 |
| EP | 0518731 | | 12/1992 |
| EP | 0519449 | | 12/1992 |
| EP | 0 611 766 | | 8/1994 |
| EP | 1 344 525 | A1 | 9/2003 |
| WO | WO 87/01706 | | 3/1987 |
| WO | WO 93/00342 | | 1/1993 |
| WO | WO 99/15525 | | 4/1999 |
| WO | WO 02/051397 | | 7/2002 |
| WO | WO 03/015778 | A1 * | 2/2003 |
| WO | WO 03/057145 | A2 | 7/2003 |
| WO | WO 03/088908 | A2 | 10/2003 |
| WO | WO 03/104230 | A1 | 12/2003 |
| WO | WO 2004/096225 | A2 * | 11/2004 |
| WO | WO 2004/096798 | | 11/2004 |
| WO | WO 2006/042954 | A1 | 4/2006 |
| WO | WO 2006/067401 | A1 | 6/2006 |
| WO | WO 2007/077394 | | 7/2007 |

OTHER PUBLICATIONS

Byrn et al., Solid-State Chemistry of Drugs, Second Edition, 1999, pp. 233-247.*
Allen et al, Discovery And SAR Of Trisubstituted Thiazolidinones As CCR4 Antagonists, Bioorganic & Medicinal Chemistry Letters, Apr. 2004, 14:1619-1624.
U.S. Appl. No. 12/146,898, filed Jun. 26, 2008, Fraisse.
Lombardino et al., Potent Antiinflammatory N-Heterocyclic 3-Carboxamides of 4-Hydroxy-2-methyl-2H-1,2-benzothiazine 1,1-Dioxide, J. Med. Chem., 16 (5) pp. 493-496 (1973).
U.S. Appl. No. 12/360,568, filed Jan. 27, 2009, Carayon.
Abdel-Magid et al, Reductive Amination of Aldehydes and Ketones by Using Sodium Triacetoxyborohydride, Tetrahedron Letters, 1990 (31) 39 pp. 5595-5598.
Abdel-Magid et al, Reductive Amination of Aldehydes and Ketones with Sodium Triacetoxyborohydride. Studies on Direct and Indirect Reductive Amination Procedures, J. Org. Chem., 1996 (61) pp. 3849-3862.
Albini et al, A Rapid in Vitro Assay for Quantitating the Invasive Potential of Tumor Cells, Cancer Research, 1987 (47) pp. 3239-3245.
Dolle et al, Synthesis and Antiviral Activity of 4-Benzyl Pyridinone Derivatives as Potent and Selective Non-Nucleoside Human Immunodeficiency Virus Type 1 Reverse Transcriptase Inhibitors, J. Med. Chem., 2000 (43) pp. 3949-3962.
Hudlicky et al, Synthesis of Dienic Acids. Application of Arndt—Eistert Reaction to Unsaturated Diazoketones, Tetrahedron Letters, 1979 (29) pp. 2667-2670.

(Continued)

*Primary Examiner*—Rebecca L Anderson
(74) *Attorney, Agent, or Firm*—Kelly L. Bender

(57) ABSTRACT

The disclosure concerns 2-carbamide-4-phenylthiazole derivatives of general formula (I). The disclosure also concerns pharmaceutical compositions containing a compound of general formula (I) and to processes for preparing and methods of using compounds of general formula (I).

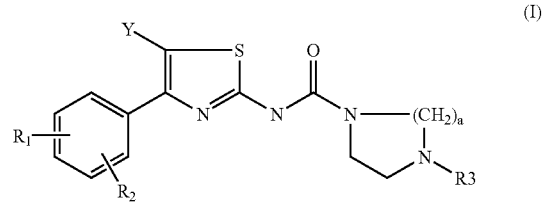

9 Claims, No Drawings

OTHER PUBLICATIONS

Paavola et al, Monomeric Monocyte Chemoattractant Protein-1 (MCP-1) Binds and Activates the MCP-1 Receptor CCR2B, J. Bio. Chem., 1998 (273) 50 pp. 33157-33165.

Taylor et al, Novel 5-Desmethylene Analogues of 5,10-Dideaza-5,6,7,8-tetrahydrofolic Acid as Potential Anticancer Agents, J. Org. Chem., 1992 (57) pp. 3218-3225.

Taylor et al, Synthesis of Pyridines by Diels-Alder Reactions of Hetero-Substituted 1,2,4-Triazines with Enamines and an Enaminone, J. Org. Chem., 1989 (54) 6 pp. 1249-1256.

Watson, Novel Methodology for the Preparation of 5-Substituted Tetrahydro[2,3-D]Pyrimidines, Synthetic Communications, 1998 (28) 10 pp. 1897-1905.

* cited by examiner

2-CARBAMIDE-4-PHENYLTHIAZOLE DERIVATIVES, PREPARATION THEREOF AND THERAPEUTIC USE THEREOF

The invention relates to 2-carbamide-4-phenylthiazole derivatives, to the preparation thereof and to the therapeutic use thereof.

A subject of the invention is compounds corresponding to formula (I) below:

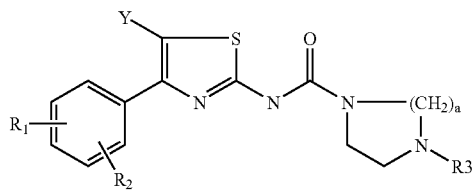

(I)

in which
(i) $R_1$ is selected from the group consisting of H, halogen, $(C_1-C_8)$alkyl, trifluoro$(C_1-C_4)$alkyl, —OH, —O—$(C_1-C_8)$alkyl, —O-trifluoro $(C_1-C_8)$alkyl, —O—$(C_3-C_{10})$cycloalkyl$(C_1-C_8)$alkyl, —O—$(C_3-C_{10})$cycloalkyl, —O—$CH_2$—$CH$=$CH_2$ and $(C_1-C_4)$alkylthio;
(ii) $R_2$ is selected from the group consisting of H, halogen, —OH, $(C_1-C_8)$alkyl, trifluoro$(C_1-C_4)$alkyl, perfluoro$(C_1-C_4)$alkyl, $(C_3-C_{10})$cycloalkyl, —O—$(C_1-C_8)$alkyl, —O—$(C_3-C_{10})$cycloalkyl$(C_1-C_8)$alkyl, —O—$(C_3-C_{10})$cycloalkyl, —O—$CH_2$—$CH$=$CH_2$ and $(C_3-C_8)$cycloalkyl$(C_1-C_8)$alkyl;
(iii) Y represents a hydrogen atom or a halogen;
(iv) $R_3$ represents:

a1) a group of formula —$(CH_2)_p$-A in which p represents 0, 1, 2, 3 or 4, and:
when p represents 2, 3 or 4, A represents a group of formula:

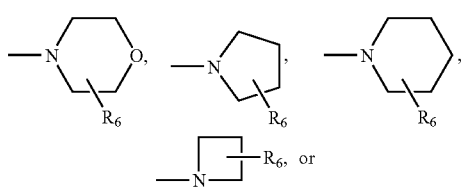

—$NR_4R_5$, in which $R_6$ is selected from the group consisting of H, F, $(C_1-C_4)$alkyl, —$(CH_2)_n$OH, —$(CH_2)_nO(C_1-C_4)$alkyl and —$(CH_2)_nNR_4R_5$, where n represents 0, 1 or 2, and $R_4$ and $R_5$ represent, independently of one another, a hydrogen atom, or a $(C_1-C_8)$alkyl, —$CO(C_1-C_4)$alkyl or —CO—O—$(C_1-C_8)$alkyl group;

or, when p represents 1, 2, 3 or 4, A represents a group of formula:

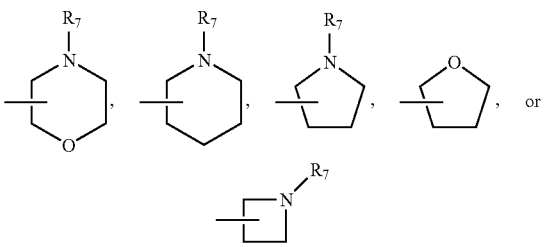

in which $R_7$ is selected from the group consisting of H, $(C_1-C_8)$alkyl, —CO—$(C_1-C_8)$alkyl, benzyl, —CO—O—$(C_1-C_8)$alkyl, —CO—O-benzyl, —CO-phenyl, —CO-heteroaryl, —CO—$(C_3-C_{10})$cycloalkyl, —$SO_2$—$(C_1-C_8)$alkyl, —$SO_2$—$(C_3-C_8)$cycloalkyl and —$SO_2$-heteroaryl;

or, when p represents 0, 1, 2, 3 or 4, A represents a group of formula:

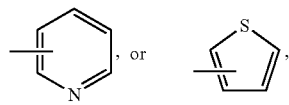

said group being optionally substituted with a $(C_1-C_4)$alkyl group;

a2) a group of formula —$(CH_2)_p$—CO-A in which p represents 1, 2, 3 or 4,
A represents a group of formula:

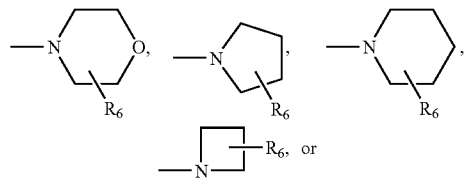

—$NR_4R_5$, in which $R_4$, $R_5$ and $R_6$ are as defined above;

a3) a group of formula —$CO(CH_2)_p$-A in which p represents 0, 1, 2, 3 or 4
when p represents 1, 2, 3 or 4, A represents a group of formula:

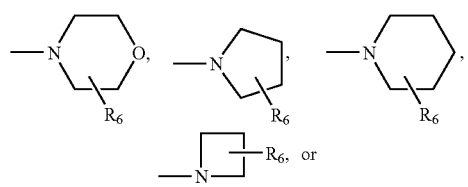

—$NR_4R_5$, in which $R_4$, $R_5$ and $R_6$ are as defined above;
or, when p represents 0, 1, 2, 3 or 4, A represents a group of formula:

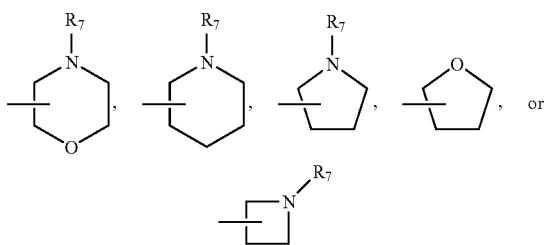

in which $R_7$ is as defined above;

or, when p represents 0, 1, 2, 3 or 4, A represents a group of formula:

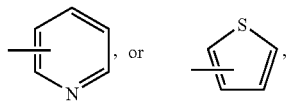

said group being optionally substituted with a $(C_1-C_4)$alkyl group;

a4) a group —B in which B represents a group of formula:

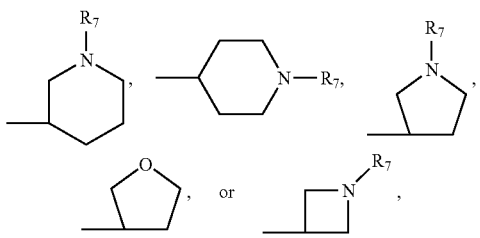

in which $R_7$ is as defined above;

(v) a represents 2 or 3.

A preferred halogen is a fluorine.

The compounds of formula (I) may contain one or more asymmetric carbon atoms. They may therefore exist in the form of enantiomers or of diastereoisomers. These enantiomers and diastereoisomers, and also mixtures thereof, including racemic mixtures, form part of the invention.

The compounds of formula (I) may exist in the form of bases or of addition salts with acids. Such addition salts form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates or of solvates, i.e. in the form of associations or combinations with one or more water molecules or with a solvent. Such hydrates and solvates also form part of the invention.

In the context of the present invention:

the term "$C_{t-z}$" where t and z may have the values of 1 to 10, is intended to mean a carbon chain that may have from t to z carbon atoms, for example the term "$C_{1-3}$" is intended to mean a carbon chain that may have from 1 to 3 carbon atoms;

the term "Hal" is intended to mean a halogen atom such as a fluorine, a chlorine, a bromine or an iodine;

the term "an alkyl group" is intended to mean a saturated, linear or branched aliphatic group optionally substituted with a halogen atom. By way of examples, mention may be made of methyl, ethyl, propyl, isopropyl, butyl, isobutyl, tert-butyl, pentyl, 2-fluoroethyl groups, etc.;

the term "a cycloalkyl group" is intended to mean a cyclic alkyl group. By way of examples, mention may be made of cyclopropyl, cyclobutyl, cyclopentyl, cyclohexyl groups, etc.;

the term "an alkoxy group" is intended to mean an —O-alkyl radical in which the alkyl group is as defined above;

the term "a heteroaryl group" is intended to mean an aryl group carrying one or more hetero atoms, optionally substituted with another hetero atom. By way of examples, mention may be made of pyrazine, pyrimidine, pyridazine, pyridine, triazine, triazole, thiazole, oxazole, pyrazole, imidazole, oxopyridine groups, etc.;

the term "a perfluoroalkyl group" is intended to mean an alkyl radical, as defined above, for which all the carbon atoms are substituted with fluorine atoms.

Among the compounds which are subjects of the invention, mention may be made of a first group of compounds of formula (I.a) below:

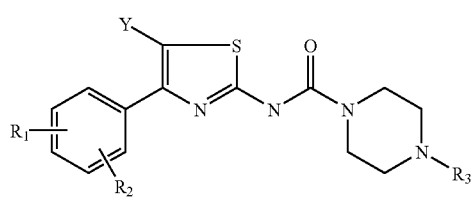

(I.a)

in which $R_1$, $R_2$, $R_3$ and Y are as defined above.

Compounds of the invention of formula (I.a) are those in which $R_1$ is in the 2-position and $R_2$ is in the 5-position with respect to the phenyl.

Among the compounds which are subjects of the invention, mention may be made of a second group of compounds of formula (I.b) below:

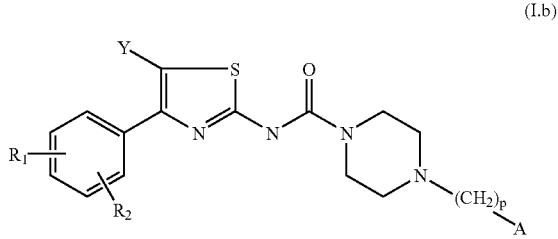

(I.b)

in which $R_1$, $R_2$, Y, p and A are as defined above.

Compounds of the invention of formula (I.b) are those in which $R_1$ is in the 2-position and $R_2$ is in the 5-position with respect to the phenyl.

Among the compounds which are subjects of the invention, mention may be made of a third group of compounds of formula (I.c) below:

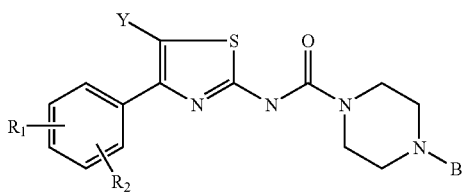

(I.c)

in which R₁, R₂, Y and B are as defined above.

Compounds of the invention of formula (I.c) are those in which R₁ is in the 2-position and R₂ is in the 5-position with respect to the phenyl.

Other compounds of the invention are those for which:
R₁ represents a —O—(C₁-C₈)alkyl group and/or;
R₂ represents a (C₁-C₈)alkyl, (C₃-C₁₀)cycloalkyl, perfluoro(C₁-C₄)alkyl or —O—(C₁-C₈)alkyl group.

Among the compounds of formula (I) of the invention, mention should in particular be made of the following compounds:

(R)—N-[4-(5-cyclohexyl-2-methoxyphenyl)thiazol-2-yl]-N'-[4-(1-methylpiperidin-3-ylmethyl)piperazin-1-yl]urea (Compound No. 76), N-[4-(2-methoxy-5-propoxyphenyl)thiazol-2-yl]-N'-[4-(2-morpholin-4-ylethyl)piperazin-1-yl]urea (Compound No. 1), N-[4-(2-methoxy-5-propylphenyl)thiazol-2-yl]-N'-[4-(3-piperidin-1-ylpropyl)piperazin-1-yl]urea (Compound No. 11), N-[4-(2-methoxy-5-propylphenyl)thiazol-2-yl]-N'-[4-(2-dimethylaminoethyl)piperazin-1-yl]urea (Compound No. 16), N-[4-(2-methoxy-5-propylphenyl)thiazol-2-yl]-N'-[4-(2-oxo-2-pyrrolidin-1-ylethyl)piperazin-1-yl]urea (Compound No. 20), N-[4-(2-methoxy-5-propylphenyl)thiazol-2-yl]-N'-[4-(2-thiophen-2-ylethyl)piperazin-1-yl]urea (Compound No. 21), N-[4-(2-methoxy-5-propylphenyl)thiazol-2-yl]-N'-[4-[2-(tetrahydrofuran-2-yl)ethyl]piperazin-1-yl]urea (Compound No. 22), N-[4-(2-methoxy-5-propylphenyl)thiazol-2-yl]-N'-[4-(2-pyrrolidin-1-ylacetyl)piperazin-1-yl]urea (Compound No. 31), N-[4-(2-methoxy-5-propylphenyl)thiazol-2-yl]-N'-[4-[2-(3-ethylaminopyrrolidin-1-yl)ethyl]piperazin-1-yl]urea (Compound No. 33), N-[4-(5-cyclohexyl-2-methoxyphenyl)thiazol-2-yl]-N'-[4-(1-methylpiperidin-4-yl)piperazin-1-yl]urea (Compound No. 47), N-[4-(5-cyclohexyl-2-methoxyphenyl)thiazol-2-yl]-N'-[4-(1-benzylpiperidin-3-yl)piperazin-1-yl]urea (Compound No. 68), N-[4-(2-methoxy-5-propylphenyl)thiazol-2-yl]-N'-[4-(2-pyridin-4-ylethyl)piperazin-1-yl]urea (Compound No. 28), N-[4-(2-methoxy-5-pentafluoroethylphenyl)thiazol-2-yl]-N'-[4-(2-pyrrolidin-1-ylethyl)piperazin-1-yl]urea (Compound No. 29), N-[4-(5-cyclohexyl-2-methoxyphenyl)thiazol-2-yl]-N'-[4-(1-isopropylpiperidin-3-yl)piperazin-1-yl]urea (Compound No. 70), N-[4-(5-cyclohexyl-2-methoxyphenyl)thiazol-2-yl]-N'-[4-(2-pyrrolidin-1-ylethyl)piperazin-1-yl]urea (Compound No. 30), N-[4-(5-cyclohexyl-2-methoxyphenyl)-5-fluorothiazol-2-yl]-N'-[4-(1-methylpiperidin-4-yl)piperazin-1-yl]urea (Compound No. 59), N-[4-(5-cyclohexyl-2-methoxyphenyl)thiazol-2-yl]-N'-[4-(2-oxo-2-pyrrolidin-1-ylethyl)piperazin-1-yl]urea (Compound No. 108), N-[4-(5-cyclohexyl-2-ethoxyphenyl)thiazol-2-yl]-N'-[4-(2-oxo-2-pyrrolidin-1-ylethyl)piperazin-1-yl]urea (Compound No. 109), N-[4-(5-cyclohexyl-2-methoxyphenyl)thiazol-2-yl]-N'-[4-(2-oxo-2-morpholino-4-ylethyl)piperazin-1-yl]urea (Compound No. 116), N-[4-(5-cyclohexyl-2-ethoxyphenyl)thiazol-2-yl]-N'-[4-(2-oxo-2-morpholino-4-ylethyl)piperazin-1-yl]urea (Compound No. 110), (S)N-[4-(5-cyclohexyl-2-methoxyphenyl)thiazol-2-yl]-N'-[4-(1-sulphomethylpiperidin-3-ylmethyl)piperazin-1-yl]urea (Compound No. 112), N-[4-(5-cyclohexyl-2-methoxyphenyl)thiazol-2-yl]-N'-[4-(1-oxo-1-(1-oxopyridin-2-yl)meth-1-ylpiperidin-3-ylmethyl)piperazin-1-yl]urea (Compound No. 113).

Some intermediates that are useful for preparing the compounds of formula (I) may also serve as a final product of formula (I), as will emerge in the examples given hereinafter.

Similarly, some compounds of formula (I) of the invention may serve as intermediates that are useful for preparing compounds of formula (I) according to the invention.

In the subsequent text, the expression "protective group Gp" is intended to mean a group that makes it possible, firstly, to protect a reactive function such as a hydroxyl or an amine during a synthesis and, secondly, to regenerate the intact reactive function at the end of synthesis. Examples of protective groups and also methods of protection and of deprotection are given in "Protective Groups in Organic Synthesis", Green et al., 2nd edition (John Wiley & Sons, Inc., New York).

In the subsequent text, the term "leaving group X" is intended to mean a group that can be readily cleaved from a molecule by breaking a heterolytic bond, with a pair of electrons leaving. This group can thus be readily replaced with another group in a substitution reaction, for example. Such leaving groups are, for example, halogens or an activated hydroxyl group such as a mesyl, tosyl, triflate, acetyl, etc. Examples of leaving groups and also references for the preparation thereof are given in "Advances in Organic Chemistry", J. March, 3rd Edition, Wiley Interscience, p. 310-316.

In the subsequent text, the expression "precursor of R₁, R₂ or R₃" is intended to mean a substituent R'₁, R'₂ or R'₃ that can be converted to R₁, R₂ and R₃ by one or more chemical reactions.

In the subsequent text, the term "group Z" is intended to mean a leaving group or a functional acid derivative, such as an acid chloride, a mixed anhydride or a symmetrical anhydride, or else the acid opportunistically activated, for example, with benzotriazol-1-yloxytris(dimethylamino)phosphonium hexafluorophosphate(BOP), O-benzotriazol-1-yl-N,N,N',N'-tetramethyluronium hexafluorophosphate (HBTU) or O-benzotriazol-1-yl-N,N,N',N'-tetramethyluronium tetrafluoroborate (TBTU).

When one or more substituents R'₁, R'₂ and/or R'₃ represent a group containing an amine or hydroxyl function, these functions can be intermediately protected: an amine function can be protected with an alkanoyl, benzyl, tert-butoxycarbonyl (Boc), benzyloxycarbonyl or 9-fluorenylmethoxycarbonyl (Fmoc) group, for example; a hydroxyl function can be protected in the form of an ether or of an ester, for example.

The compounds of the invention can be prepared according to various methods described in the present patent application.

Before tackling these methods, the methods for preparing the aminothiazole derivatives of formula (II) and the methods for preparing the amine derivatives of formula (III), which are useful for preparing the compounds of formula (I) of the invention, are described below.

The aminothiazole derivatives of formula (II) can be prepared by known methods such as those described in documents EP 518 731, EP 611 766 and WO 99/15525.

In general, when Y=H, thiourea is reacted with a halogenated ketone of formula 1 according to the following reaction scheme:

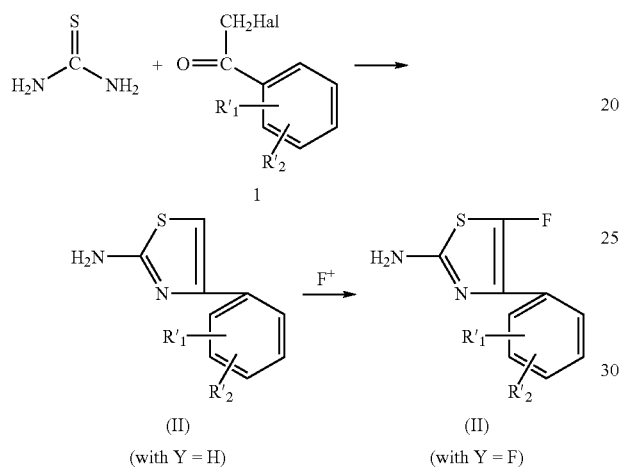

(II)
(with Y = H)

(II)
(with Y = F)

The substituents $R'_1$ and $R'_2$ have the values indicated above, i.e. $R'_1$ and $R'_2$ represent, respectively, $R_1$ and $R_2$ as defined for the compound of general formula (I) or groups that are precursors of $R_1$ and $R_2$; Hal represents a halogen atom, preferably bromine, chlorine or iodine.

As indicated on the above scheme, the compounds of type (II) with Y=H, $R'_1$ and $R'_2$ having the values indicated above, can be converted into compounds of type (II) with Y=F and $R'_1$ and $R'_2$ having the values indicated above, by reaction with a fluorination agent, for example Selectfluor©, in a solvent such as DMF or DCM at a temperature ranging from 0° C. to 50° C.

The halogenated ketones of formula 1 can be prepared by processes known to those skilled in the art. For example, the bromoketones can be obtained by reacting bromine, cupric bromide or phenyltrimethylammoniumtribromide (PTT) with an acetophenone derivative of formula:

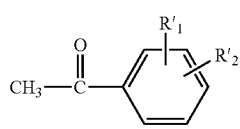

2 in which $R'_1$ and $R'_2$ have the values indicated above, in an organic solvent such as ethyl acetate, a chlorinated solvent or a mixture thereof, or else an alcohol.

When the acetophenone derivative of formula 2 is not commercially available, it can be prepared by various methods:

a Friedel-Crafts reaction with benzene substituted with $R'_1$ and $R'_2$, which is reacted with acetyl chloride or acetic anhydride, in the presence of a Lewis acid such as $AlCl_3$ or $TiCl_4$, for example;

the action of acetyl chloride, in the presence of palladium, with benzene substituted with $R'_1$ and $R'_2$, after deprotonation of the benzene, for example by the action of butyllithium and then addition of zinc chloride or of manganese iodide. This procedure can be used to prepare an acetophenone derivative of formula 2 in which $R'_2=R_2=(C_1-C_4)$perfluoroalkyl;

a Fries rearrangement: from an acetoxybenzene derivative of formula:

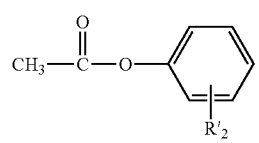

3 by the action of a Lewis acid, a hydroxyacetophenone derivative is obtained, of formula:

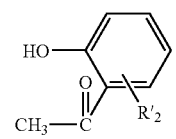

4

The hydroxyl function corresponds to a group $R'_1$ which can be converted, in a subsequent step, to a group —O—W such as —O—$(C_1-C_8)$alkyl, trifluoromethoxy, trifluoroethoxy, allyloxy, $(C_3-C_{10})$cycloalkylmethoxy or $(C_3-C_{10})$ cycloalkyloxy.

The conversion of $R'_1$ to $R_1$ can be carried out either on the aminothiazole of formula (II), or on a compound of formula (I).

The benzene derivatives substituted with $R'_1$ and $R'_2$ are commercially available or are prepared by methods known to those skilled in the art.

For example, to prepare a compound in which $R_1$ is a group —O—W as defined above, the following procedure is carried out:

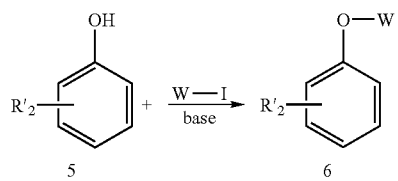

A halobenzene derivative can also be substituted according to the scheme below:

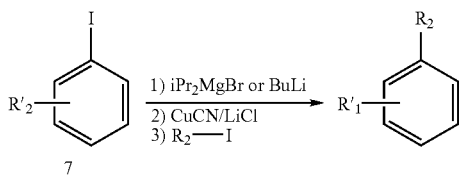

In the specific case where $R_2$ represents a $(c_1$-$c_4)$perfluoroalkyl, the procedure can also be carried out according to the reaction scheme below:

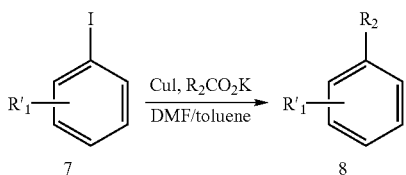

A subject of the invention is also the compounds of formula (II.a):

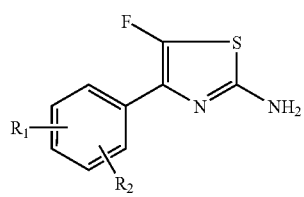

in which:
- $R_1$ represents a halogen atom, or an —O—$(C_1$-$C_8)$alkyl or $(C_3$-$C_{10})$cycloalkyl$(C_1$-$C_8)$alkoxy group;
- $R_2$ represents a $(C_1$-$C_8)$alkoxy, $(C_1$-$C_8)$alkyl, $(C_3$-$C_{10})$cycloalkyl, trifluoro$(C_1$-$C_4)$alkyl or perfluoro$(c_1$-$c_4)$alkyl group.

Examples of preparation of aminothiazole derivatives of formula (II) are given in the subsequent text.

The amine derivatives of formula (III) are known or can be prepared according to the methods described in particular in document WO 87/01706 or according to the methods described in the subsequent text.

In the subsequent text, the group A' represents a group that is a precursor of the group A or a group A as defined above.

The compounds of formula (III) in which $R'_3$ represents a precursor group of $R_3$ or a group $R_3$ as defined above, and in which a is as defined above, are obtained from compounds of formula 9 by deprotection of the nitrogen of the piperazine or of the homopiperazine, protected according to methods known to those skilled in the art or described in the literature (WO 03/104230 and WO 03/057145).

By way of example, the procedure may be carried out as follows:

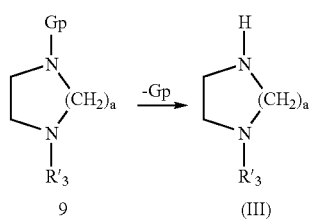

The compounds of formula 9 are commercial or can be synthesized from commercial compounds, according to methods known to those skilled in the art.

Preparation 2.1

The compounds of formula 9 in which $R'_3$ is a precursor group of $R_3$, with $R_3$ representing a group —$(CH_2)_p$-A, in which A represents:

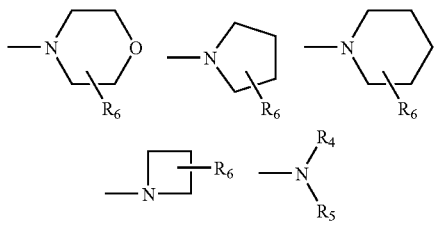

and p is 2, 3 or 4, $R_4$, $R_5$ and $R_6$ being as defined above, can be prepared by reaction of the compound 10 with A'H in the presence of a base such as $K_2CO_3$, triethylamine or caesium carbonate in a solvent such as THF, acetonitrile, toluene or DMF, at temperatures ranging from 0° C. to 150° C., so as to obtain the compound 11. The compound 11 can then be converted to a compound of formula 9 by reduction of the amide function, for example with $LiAlH_4$, diisobutylaluminium hydride (Dibal), $BH_3$ in THF, ether or toluene, at a temperature of between 0° C. and 70° C., so as to give the compound of formula 9 in which $R_3$ represents —$(CH_2)_p$-A:

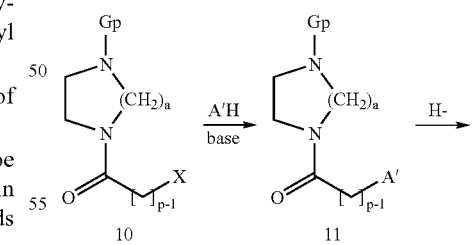

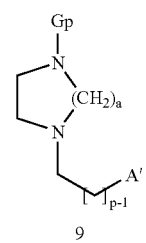

The compound of formula 10 can be prepared by reaction of a monoprotected piperazine or homopiperazine with a reactant of formula 12 below:

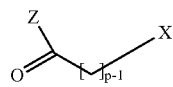

in which Z represents a leaving group or a group derived from the activation of a carboxylic acid function and X represents a leaving group, in a solvent such as THF, acetonitrile, DMF, or dichloromethane in the presence of a base such as $K_2CO_3$ or triethylamine and, when Z represents an —OH group, of a reactant that activates the acid function, such as BOP, TBTU or CDI, according to the scheme below:

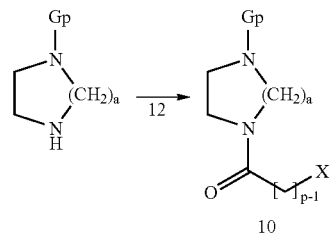

Preparation 2.2

The compounds of formula 9 in which $R'_3$ is a precursor group of $R_3$, with $R_3$ representing a —$(CH_2)_p$-A in which A represents:

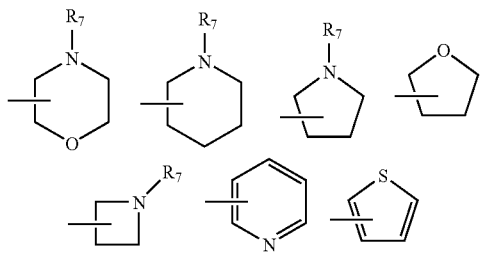

and p represents 1, 2, 3 or 4, $R_7$ being as defined above, can be prepared by reaction of the compound 13 with a monoprotected piperazine or homopiperazine in a solvent such as THF, acetonitrile, DMF or dichloromethane in the presence of a base such as $K_2CO_3$ or triethylamine and, when Z represents an —OH group, of a reactant that activates the acid function, such as BOP, TBTU or CDI, according to the scheme below:

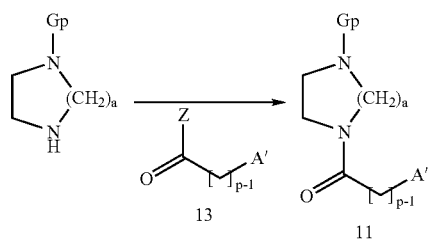

The compound 11 obtained can then be converted to a compound of formula 9 according to the scheme described above.

The compound 13, when it is not commercially available, can be obtained by homologation of the commercial carboxylic acid according to conventional methods such as reactions of Arndt-Eistert type (Tetrahedron Lett., 1979, 29, 2667; "Advances in Organic Chemistry", J. March, 3rd Edition, Wiley Interscience, p. 1405-1407), according to the scheme below:

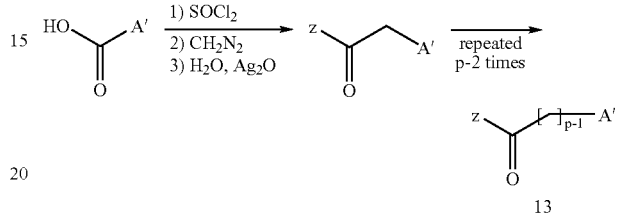

Preparation 2.3

The compounds of formula 9 in which $R'_3$ represents a group that is a precursor of the group $R_3$, with $R_3$ representing —$(CH_2)_p$CO-A as defined above, can be obtained from the compounds of formula 14 in which Z is as defined above, by reaction with A'H in the presence of a base such as $K_2CO_3$, triethylamine or caesium carbonate and, when Z represents an —OH group, of a reactant that activates the acid function, such as BOP, TBTU or CDI, in a solvent such as, for example, THF, acetonitrile or DMF, at temperatures ranging from 0° C. to 150° C., according to the scheme below:

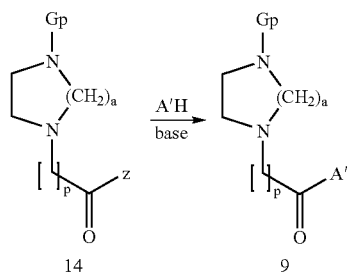

The compounds of formula 14, when they are not commercially available, can be obtained from a monoprotected piperazine or homopiperazine and the reactant 15 in which Z is as defined above, by acylation or peptide-type coupling in the presence of a base such as $K_2CO_3$, triethylamine or caesium carbonate or of a coupling reactant such as BOP, TBTU or CDI, in a solvent such as, for example, THF, acetonitrile or DMF, at temperatures ranging from 0° C. to 150° C., according to the scheme below:

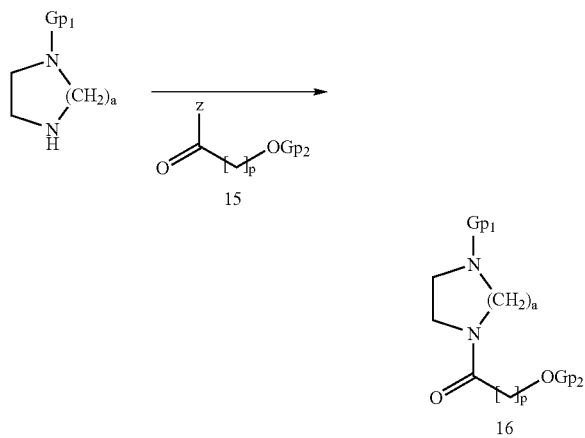

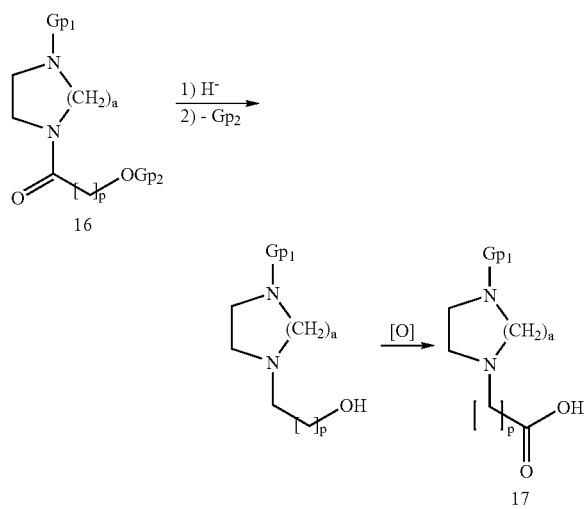

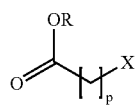

The compound 16 is then converted by reduction of the amide function with, for example, LiAlH$_4$ in THF or ethyl ether at a temperature of between 0 and 50° C. The intermediate obtained is deprotected and then oxidized to the carboxylic acid 17, for example with CrO$_3$ or with other reactants according to the methods described in "Advances in Organic Chemistry", J. March, 3rd Edition, Wiley Interscience, p. 1537-1539, according to the scheme below:

The compound 17 is then optionally converted so as to give a compound of formula 14, or is used in its acid form (Z=OH).

Alternatively, the compounds of formula 17 can be prepared by reaction of monoprotected piperazine or homopiperazine with a reactant 18 of formula:

in which X is as defined above and R represents a (C$_1$-C$_4$) alkyl group, by alkylation of the nitrogen in the presence of a base such as K$_2$CO$_3$, triethylamine or caesium carbonate in a solvent such as THF, acetonitrile, toluene or DMF, at temperatures ranging from 25 to 150° C., according to the scheme below:

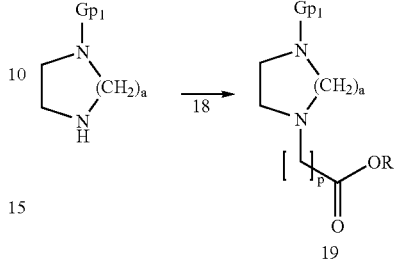

The compound 19 obtained is then converted to the acid of formula 17 by saponification or acid hydrolysis or any other method known to those skilled in the art.

Preparation 2.4

The compounds of formula 9 in which R'$_3$ represents a group that is a precursor of the group R$_3$, with R$_3$ representing a group —CO(CH$_2$)$_p$-A, in which A represents:

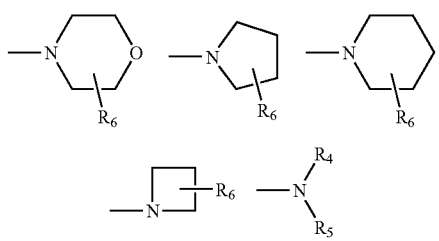

and p representing 1, 2, 3 or 4, and R$_4$, R$_5$ and R$_6$ being as defined above, can be prepared using the method described in preparation 2.1 above.

Preparation 2.5

The compounds of formula 9 in which R'$_3$ represents a group that is a precursor of the group R$_3$, with R$_3$ representing a group —CO(CH$_2$)$_p$-A, in which A represents:

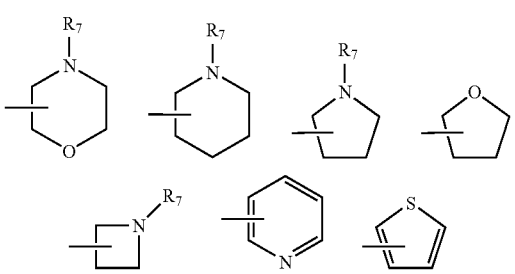

and p representing 0, 1, 2, 3 or 4, and $R_7$ being as defined above, can be prepared using the method described in preparation 2.1 above.

Preparation 2.6

The compounds of formula 9 in which $R'_3$ represents a group that is a precursor of the group $R_3$, with $R_3$ representing a group —B, can be prepared by reaction of a monoprotected piperazine or homopiperazine and of a ketone B' that is a precursor of B, by means of a reductive amination reaction in the presence of a reducing agent such as $NaHB(OAc)_3$, $NaBH_3CN$ in a solvent such as 1,2-dichloroethane, dichloromethane or THF at temperatures ranging from 0° C. to 70° C. (Synth. Commun., 1998, 28 (10), 1897-1905, J. Org. Chem., 1992, 57 (11), 3218-3225, J. Org. Chem., 1996, 61, 3849-3862, Tetrahedron Lett., 1990, 31, 5595-5598), according to the scheme below:

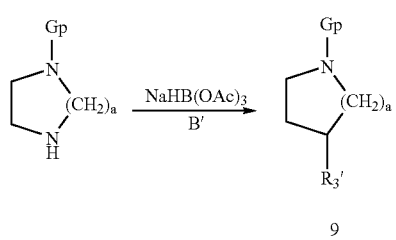

9

The ketones B' used are commercial or can be synthesized according to the method described in J. Org. Chem., 1989, 54, 1249-1256.

The compounds of formula (I) of the invention can be prepared according to general scheme 1 below:

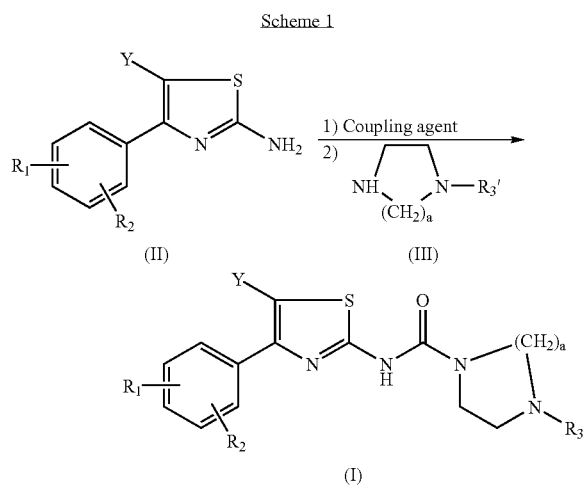

According to scheme 1, the compounds of the invention are obtained by coupling the aminothiazole derivative of formula (II) in which $R_1$, $R_2$ and Y are as defined above, with an amine derivative of formula (III) in which $R'_3$ represents a precursor group of $R_3$ or a group $R_3$ as defined above, and a is as defined above.

According to scheme 1, the aminothiazole derivative of formula (II) is placed in the presence of a coupling agent for a period of 2 to 16 hours, and then with the amine derivative of formula (III) for a period of 0.5 to 4 hours.

The coupling agent can be chosen from those that are known to those skilled in the art, for example phosgene, di-(N-succinimidyl)carbonate or 1,1'-carbonyldiimidazole, according to the methods described in "Encyclopedia of Reagents for Organic Synthesis", L. A. Paquette, volume 2, p. 1006; volume 4, p. 2304; volume 6, p. 4107.

The reaction can be carried out in various solvents, for example dichloromethane, dimethylformamide or toluene, in the presence of a base such as triethylamine or $K_2CO_3$, at a temperature ranging from 0° C. to 100° C.

The compounds of the invention of formula (I) in which $R_3$ represents a group —$CO(CH_2)_p$-A (or —$CO(CH_2)_p$-A') in which A and p are as defined above and A' represents a precursor group of A, can also be prepared according to scheme below:

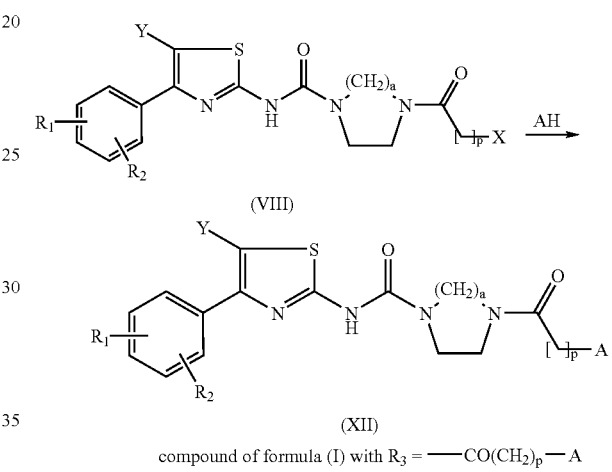

compound of formula (I) with $R_3$ = —$CO(CH_2)_p$—A

According to scheme 2, the aminothiazole derivative of formula (VIII) in which $R_1$, $R_2$, Y, a and p are as defined above and X represents a leaving group is reacted with a group A'H that is a precursor of the group A or a group AH as defined above, to give the compound of formula (XII) (compound of formula (I) in which $R_3$ represents a group —$CO(CH_2)_p$-A).

The reaction is carried out in a solvent such as tetrahydrofuran or dimethylformamide in the presence of a base such as triethylamine or $K_2CO_3$, at temperatures ranging from ambient temperature to 150° C., for a period of 1 to 24 hours.

The compounds of the invention of formula (I) in which $R_3$ represents a group —$(CH_2)_p$-A can be prepared in the known manner, from the compound of formula (XII) as defined above, directly by reduction of the carbonyl function with a reducing agent such as Red-Al or $LiAlH_4$ according to scheme 3 below:

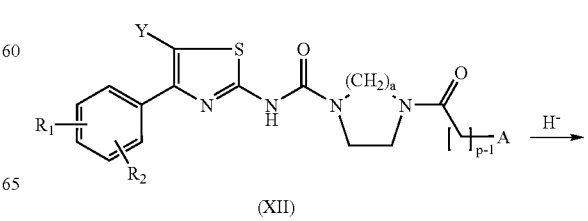

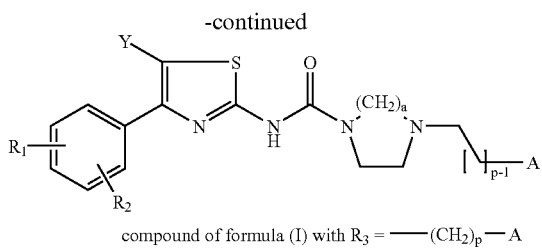

compound of formula (I) with $R_3 = -(CH_2)_p-A$

Alternatively, the compounds of formula (I) can be prepared from the compound of formula (XII) in which the group A is protected prior to the reducing reaction, in particular when the group A contains functions that are incompatible with the type of reducing agent used. After reduction, a compound of formula (I) is then obtained by deprotection of the group A and optional functionalization of the group A.

The compounds of formula (VIII) can be prepared according to scheme 4 below:

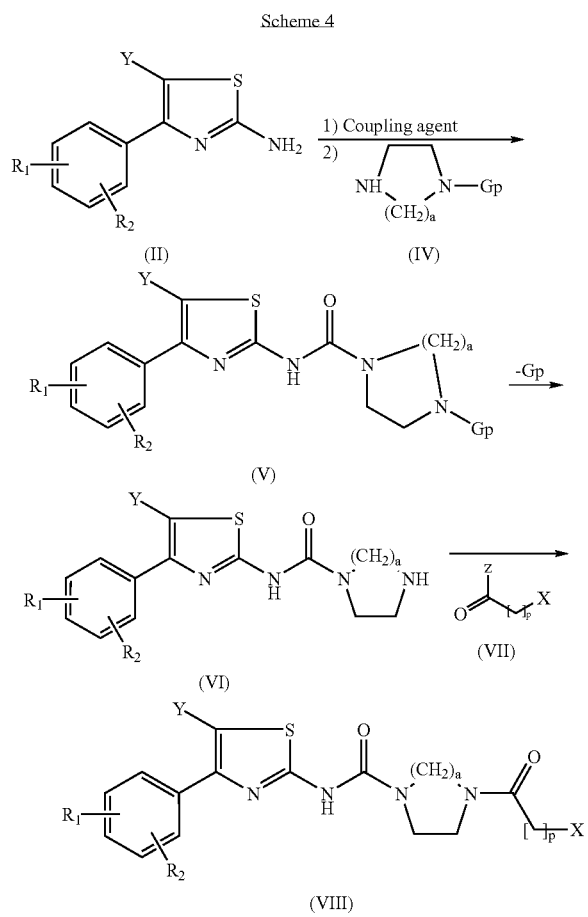

According to scheme 4, the aminothiazole derivative of formula (II) as defined above is coupled to an amine derivative of formula (IV) in which Gp represents a protective group, for example a benzyl or Boc group, and a is as defined above, to give the compound of formula (V).

The reaction is carried out under the same conditions as those described above for scheme 1.

The compound of formula (V) is then deprotected, according to the methods known to those skilled in the art, to give the compound of formula (VI), which is reacted with the compound of formula (VII) in which Z represents a leaving group or a group derived from the activation of a carboxylic acid function and X represents a leaving group, to give the compound of formula (VIII) in which $R_1$, $R_2$, Y, X and a are as defined above.

Alternatively, the compounds of formula (VIII) can be prepared according to scheme 5 below.

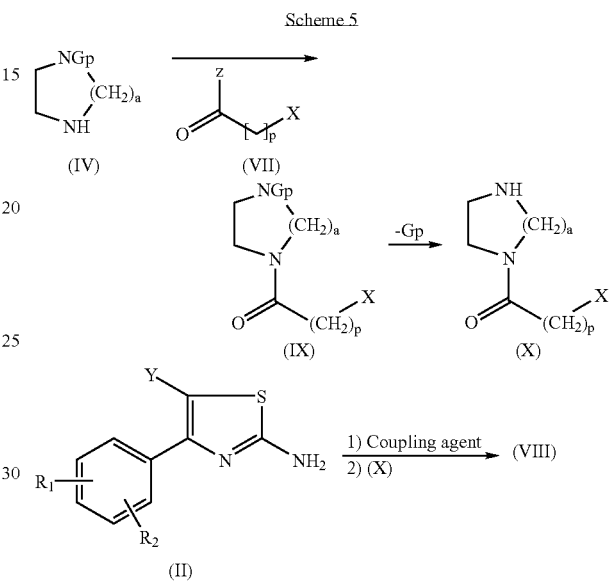

According to scheme 5, the compound of formula (VII) in which X is as defined above and Z represents a leaving group or a group derived from the activation of a carboxylic acid function can be coupled to the compound of formula (IV) by acylation or peptide-type coupling in the presence of a base such as $K_2CO_3$, triethylamine or caesium carbonate or of a coupling reactant such as BOP, TBTU or CDI, in a solvent such as, for example, THF, acetonitrile or DMF, at temperatures ranging from 0° C. to 150° C. The compound (IX) is thus obtained. The compound (X), obtained by deprotection of the compound (IX), is then coupled with an aminothiazole compound of formula (II) under conditions identical to those of scheme 1.

In the general synthesis schemes, the starting compounds and the reactants, when the method for preparing them is not described, are commercially available or are described in the literature, or else can be prepared according to methods that are described therein or that are known to those skilled in the art.

The examples that follow describe the preparation of compounds in accordance with the invention. These compounds are not limiting and merely illustrate the present invention. The numbers of the compounds exemplified refer to those given in Table II, which illustrates the chemical structures and the physical properties of some compounds according to the invention.

In the preparations and examples that follow:
CyHex=a cyclohexyl group;
AT=ambient temperature;
DCM=dichloromethane
DSC=di-(N-succinimidyl)carbonate DIPEA=diisopropylethylamine
THF=tetrahydrofuran
BOP=benzotriazol-1-yloxytris(dimethylamino)phosphonium hexafluorophosphate
Mp=melting point
CDI=1,1'-carbonyldiimidazole
DMF=dimethylformamide
DCE=dichloroethane
TFA=trifluoroacetic acid
Red-Al®=sodium bis(2-methoxyethoxy)aluminium hydride
TBME=tert-butyl methyl ether
TBTU=2-(1H-benzotriazol-1-yl)-1,1,3,3-tetramethyluronium tetrafluoroborate Preparation of Aminothiazole Derivatives of Formula (II)

Compounds of formula (II) in which:
Y represents —H (preparations 1.1 to 1.25),
$R_1$ and $R_2$ are in the 2-position and 5-position, respectively, with respect to the phenyl.

Preparation 1.1

4-(2-Methoxy-5-propoxyphenyl)-1,3-thiazol-2-amine

A) 1-(2-Hydroxy-5-propoxyphenyl)ethanone 10 g of 2,5-dihydroxyacetophenone suspended in 100 ml of acetone are placed in a 500 ml round-bottomed flask, and 9.14 g of anhydrous $K_2CO_3$ are added, followed by 12.4 g of propyl iodide. The reaction medium is refluxed for 30 hours. After a return to ambient temperature, the medium is filtered through Celite® and then concentrated. The brown oil obtained is taken up in EtOAc, filtered, and washed with water, with a 2M HCl solution and then with a saturated NaCl solution. The organic phase is evaporated off to give a black paste. The paste is taken up in chloroform and filtered. The medium is concentrated to give 11.4 g of a black solid. The latter is taken up in absolute ethanol. The solution is placed in a freezer for 10 minutes, and a solid precipitates and is collected by filtration. The filtrate is concentrated, taken up in ethanol, cooled in a freezer, and then filtered again. This operation is repeated 4 times to give 8.35 g of the expected compound in the form of a powder.

B) 1-(2-Methoxy-5-propoxyphenyl)ethanone 49.8 g of $K_2CO_3$ followed by 22.4 ml of methyl iodide are added to a solution of 35 g of the solid above in 350 ml of DMF. The reaction medium is heated for 12 hours at 60° C. After a return to ambient temperature, the medium is filtered through Celite®, diluted in ether and washed with a 2M HCl solution. The aqueous phase is extracted twice in ether. The combined organic phases are washed with a dilute sodium hydroxide solution, and then washed with water, twice, and with a saturated NaCl solution. The organic phase is dried over $MgSO_4$, and then evaporated to give 35.55 g of a brown oil. The oil is distilled under reduced pressure at 115° C., to give 32.8 g of the expected compound in the form of an oil.

C) 2-Bromo-1-(2-methoxy-5-propoxyphenyl)ethanone 4.8 ml of bromine are added dropwise to a solution of 16.4 g of the oil obtained in the previous step, in 100 ml of methanol. The medium is stirred for 30 minutes at ambient temperature and then evaporated. The oil obtained is taken up in dichloromethane, washed 3 times in water, then dried over $MgSO_4$ and evaporated to give 24.5 g of a brown oil.

D) 4-(2-Methoxy-5-propoxyphenyl)-1,3-thiazol-2-amine 24.5 g of thiourea are added to a solution of 42 g of the bromoketone prepared in the previous step, in 200 ml of ethanol. The medium is refluxed for 1 hour 30 minutes. The medium is then placed in a refrigerator for 12 hours, and then filtered. The solid thus collected is rinsed with a small amount of cold ethanol, and then with ether. 25 g of hydrobromide are recovered.

The solid is suspended in a water/dichloromethane mixture and a return to the base is achieved by adding sodium hydroxide. The aqueous phase is extracted twice in dichloromethane. The combined organic phases are dried over $MgSO_4$ and then evaporated. The oil obtained is chromatographed on silica gel, to give 12 g of the expected product in the form of a powder.
Mp=76° C.

Preparation 1.2

4-(5-Butyl-2-methoxyphenyl)-1,3-thiazol-2-amine

A) 4-Butylphenyl acetate

A solution of 10 g of 4-n-butylphenol, 10 ml of $Ac_2O$ and 8 ml of pyridine is stirred at reflux in 10 ml of dichloromethane. After 2 hours, the medium is cooled to ambient temperature, diluted in dichloromethane, washed with water, washed with a 1M HCl solution, washed in a saturated $CuSO_4$ solution, washed with water, and dried over $MgSO_4$. After evaporation, 10.8 g of the expected compound are recovered in the form of an oil.

B) 1-(5-Butyl-2-hydroxyphenyl)ethanone 3.22 g of $AlCl_3$ are added, in several portions, to 5 g of the oil obtained in the previous step, in a 100 ml round-bottomed flask. The medium is heated at 130° C. for 1 hour. After a return to ambient temperature, a solution of ice-cold water acidified with 35% HCl is run into the reaction crude. The medium is placed in an ultrasound bath. EtOAc is added so as to obtain solubilization of the medium after 15 minutes. The aqueous phase is extracted 3 times in EtOAc, and the organic phases are washed with water and then with a saturated NaCl solution. After drying over $MgSO_4$ and evaporation, 4.5 g of a yellow oil are recovered.

C) 1-(5-Butyl-2-methoxyphenyl)ethanone 1.44 g of $K_2CO_3$ followed by 0.648 ml of methyl iodide are added to a solution of 1 g of the oil obtained in the previous step, in 10 ml of DMF. The medium is heated at 60° C. overnight. After a return to ambient temperature, the medium is filtered through Celite®, diluted in ether and washed with a 2M HCl solution. The aqueous phase is extracted twice in ether. The combined organic phases are washed with a dilute sodium hydroxide solution and then washed with water, twice, and with a saturated NaCl solution. The organic phase is dried over $MgSO_4$ and then evaporated, to give 1.27 g of a brown oil. The oil is purified by chromatography, to give 0.66 g of the expected compound.

D) 4-(5-Butyl-2-methoxyphenyl)-1,3-thiazol-2-amine 0.19 ml of bromine is added to a solution of 0.66 g of the product of the previous step, in 10 ml of methanol. The medium is stirred for 10 minutes, and then evaporated and taken up in dichloromethane. The organic phase is washed 3 times with water, and then dried over $MgSO_4$. 0.79 g of the expected product is recovered after evaporation. This compound is dissolved in 5 ml of ethanol in the presence of 0.46 g of thiourea and the medium is refluxed for 2 hours 30 minutes. A solid precipitates during the return to ambient temperature. The solid thus collected is rinsed with a small amount of cold ethanol and then with ether. 0.6 g of the hydrobromide is thus recovered.

The solid is suspended in a water/dichloromethane mixture and a return to the base is achieved by adding sodium hydroxide. The aqueous phase is extracted twice in dichloromethane. The combined organic phases are dried over $MgSO_4$ and then evaporated, to give 0.34 g of a yellow oil that crystallizes slowly. The mother liquors are evaporated and then stirred in a water/dichloromethane mixture and a return to the base is achieved by adding sodium hydroxide. The aqueous phase is extracted twice in dichloromethane. The combined organic phases are dried over $MgSO_4$ and then evaporated. The oil obtained is chromatographed on silica gel, to give 0.18 g of the expected compound.

Mp=48° C.

Preparation 1.22

4-(5-Pentafluroethyl-2-methoxyphenyl)-1,3-thiazol-2-amine

A) 1-Methoxy-4-pentafluoroethylbenzene 8.3 g of potassium pentafluoropropionate and 9.8 g of CuI are introduced, under an inert atmosphere, into a 500 ml three-necked flask equipped with a Dean-Starck apparatus and a condenser. 90 ml of DMF and 110 ml of toluene are added. The medium is heated to 140° C. under nitrogen; 80 ml of toluene are distilled. The medium is then cooled to AT and then deoxygenated with nitrogen bubbling. 6 g of iodoanisole are then added and the medium is heated at 155° C. for 20 h. After a return to AT, the medium is diluted in 200 ml of a water/ethyl ether mixture. The medium is then filtered through Celite®. The organic phase is washed 3 times with water, dried over $MgSO_4$ and then evaporated, to give 4.3 g of a brown oil.

B) 1-(2-Methoxy-5-pentafluoroethylphenyl)ethanone 7.4 ml of BuLi at 2.5M in hexane are added, at –70° C., to a solution of 3.5 g of 1-methoxy-4-pentafluoroethylbenzene in 50 ml of anhydrous THF. The medium is stirred at –70° C. for 30 min and then at 0° C. for 45 min. 15.5 ml of a 1M solution of zinc chloride in ether are then added. After stirring at 0° C. for 10 min, 1.33 ml of acetyl chloride are added. The medium is then deoxygenated with nitrogen, and 332 mg of palladium benzyl(chloro)bis(triphenylphosphine) in 5 ml of anhydrous THF are introduced. The medium is stirred at 0° C. for 2 h 30 min and then at AT for 72 hours. The medium is run into a 2.5M HCl solution and then extracted in ether. The organic phase is washed with $NaHCO_3$ at 5% in water, with water, and then with a saturated NaCl solution. After drying over $MgSO_4$ and evaporation, the crude is purified by flash chromatography on silica, to give 2.25 g of a white solid.

Mp=47° C.

C) 4-(2-Methoxy-5-pentafluorophenyl)thiazol-2-ylamine 0.5 ml of bromine in solution in 8 ml of methanol is added to a solution of 2.25 g of the product obtained in the previous step, in 10 ml of methanol. The medium is stirred for 10 min and then evaporated and taken up in dichloromethane. The organic phase is washed 3 times with water and then dried over $MgSO_4$. 2.63 g of the brominated product are obtained after evaporation. This compound is dissolved in 15 ml of methanol in the presence of 1.25 g of thiourea, and the medium is refluxed for 2 h. A solid precipitates during the return to AT. The solid thus collected is rinsed with ethyl ether. The solid is suspended in a water/dichloromethane mixture and a return to the base is achieved by adding sodium hydroxide. The aqueous phase is extracted twice in dichloromethane. The combined organic phases are dried over $MgSO_4$ and then evaporated, to give 1.63 g of a yellow solid.

Mp=125° C.

Preparation 1.3

4-(5-Cyclohexyl-2-methoxyphenyl)-1,3-thiazol-2-amine

A) 7.84 g of $K_2CO_3$ followed by 3.53 ml of methyl iodide are added to a solution of 5 g of 4-cyclohexylphenol in 60 ml of DMF. The medium is heated at 60° C. overnight. After a return to ambient temperature, the medium is filtered through Celite®, and then diluted in ether and hydrolysed with water. The aqueous phase is acidified and then extracted in 3 times 50 ml of ether. The combined organic phases are washed with a dilute sodium hydroxide solution, and then washed with water, twice, and with a saturated NaCl solution. The organic phase is dried over $MgSO_4$ and then evaporated, to give 4.31 g of the expected compound in the form of a solid.

Mp=67° C.

B) 1-(5-Cyclohexyl-2-methoxyphenyl)ethanone

A suspension of 5.6 g of $AlCl_3$ in 40 ml of dichloromethane is cooled to –10° C. 3 ml of AcCl and 4 g of the compound of the previous step are added. The medium is stirred for 1 hour at –10° C., and then poured into a beaker containing ice mixed with 35% HCl. After separation by settling out, the combined organic phases are dried over $MgSO_4$ and then evaporated, to give 4.54 g of the expected product.

C) 4-(5-Cyclohexyl-2-methoxyphenyl)-1,3-thiazol-2-amine 1.16 ml of bromine are added, dropwise, to a solution of 4.5 g of the product of the previous step, in 25 ml of methanol. The medium is stirred at ambient temperature for 30 minutes, and then becomes very viscous. 5 ml of methanol are added, followed by 3.23 g of thiourea. The medium is refluxed for 2 hours. After a return to ambient temperature, a solid precipitates. The solid is collected, and then rinsed with a small amount of cold methanol. The solid is suspended in a water/dichloromethane mixture and a return to the base is achieved by adding sodium hydroxide. The aqueous phase is extracted twice in dichloromethane. The combined organic phases are dried over $MgSO_4$ and then evaporated, to give 3.33 g of the expected compound in the form of a solid.

Mp=113° C.

Preparation 1.4

4-(2-Methoxy-5-propylphenyl)-1,3-thiazol-2-amine

A) 1-(2-Methoxy-5-propylphenyl)ethanone

A suspension of 10.6 g of $AlCl_3$ in 150 ml of dichloromethane is cooled to –10° C. 5.7 ml of AcCl and 6 g of 4-propylanisole are added. The medium is stirred at –10° C. for 30 min, and then poured into a beaker containing ice mixed with 35% HCl. After separation by settling out, the aqueous phase is extracted 3 times in dichloromethane, and the combined organic phases are washed with water and with a saturated NaCl solution, dried over $MgSO_4$ and then evaporated, to give 7.86 g of a brown oil (quant.).

B) 2-Bromo-1-(2-methoxy-5-propylphenyl)ethanone 2.46 ml of bromine diluted in 40 ml of methanol are added, dropwise, to a solution of 7.86 g of the compound obtained in the previous step, in 80 ml of methanol. The medium is stirred at AT for 30 min, and then evaporated. The oil obtained is taken up in dichloromethane, washed 3 times in water and then dried over $MgSO_4$ and evaporated, to give 11.25 g (quant.) of a yellow oil.

C) 4-(2-Methoxy-5-propylphenyl)-1,3-thiazol-2-amine 4.94 g of thiourea are added to a solution of 8 g of the compound obtained in the previous step, in 60 ml of ethanol. The medium is refluxed for 1 h 30 min. The medium is then placed in a refrigerator for 12 h and then filtered. The solid thus collected is rinsed with a small amount of cold ethanol and then with ether. The procedure is repeated a second time. The solid is suspended in a water/dichloromethane mixture and a return to the base is achieved by adding sodium hydroxide. The aqueous phase is extracted twice with dichloromethane. The combined organic phases are dried over $MgSO_4$ and then evaporated, to give 4.89 g of a brown oil that crystallizes slowly (67%).

The mother liquors are evaporated and then stirred in a water/dichloromethane mixture and a return to the base is achieved by adding sodium hydroxide. The aqueous phase is extracted twice in dichloromethane. The combined organic phases are dried over $MgSO_4$ and then evaporated. The oil obtained is chromatographed on silica gel, to give 580 mg of the expected product.

Yield (total): 75%

Mp=84° C.

The compounds of formula (II) described in Table I below are prepared according to the procedures above.

TABLE I

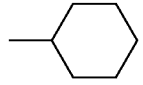

(II)

| Preparation No. | $R_1$ | $R_2$ | Salt | Mp(° C.) M |
|---|---|---|---|---|
| 1.1 | —OMe | -OPr | — | Mp = 76° C. |
| 1.2 | —OMe | -nBu | — | Mp = 48° C. |
| 1.2a | —OMe | -nBu | — | Mp = 186° C. |
| 1.3 | —OMe | 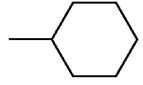 | — | Mp = 113° C. |
| 1.4 | —OMe | -nPr | — | Mp = 84° C. |
| 1.5 | —OEt | -Et | — | Mp = 83° C. |
| 1.6 | —OMe | -Et | — | Mp = 100° C. |
| 1.7 | —OEt | 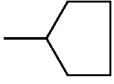 | — | Mp = 110° C. |
| 1.8 | —OMe | 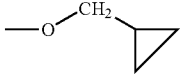 | — | Mp = 110° C. |
| 1.9 | —OEt | -nBu | — | Mp = 65° C. |
| 1.10 | —OMe | $CF_3$ | — | Mp = 144° C. |
| 1.11 | —OMe | -iPr | — | Mp = 109° C. |
| 1.12 | —OMe | -Me | — | Mp = 121° C. |
| 1.13 | —O-CH$_2$-▷ | -nBu | — | Mp = 59° C. |

TABLE I-continued (II)

| Preparation No. | $R_1$ | $R_2$ | Salt | Mp(° C.) M |
|---|---|---|---|---|
| 1.14 | —OMe | —CH(CH$_2$—CH$_3$)(CH$_2$—CH$_3$) | — | Mp = 91–93° C. |
| 1.16 | —Cl | CF$_3$ | — | Mp = 110° C. |
| 1.17 | —OEt | Me | — | Mp = 124° C. |
| 1.18 | —OMe | —CH(nPr)$_2$ | HCl | MH$^+$= 305.4 t = 7.61 |
| 1.19 | -OnPr | -nBu | — | Mp = 63° C. |
| 1.20 | —OMe | -nHex | — | Mp = 43° C. |
| 1.21 | —OEt | -nHex | — | Mp = 75° C. |
| 1.22 | —OMe | CF$_3$CF$_2$ | — | Mp = 125° C. |
| 1.23 | —OEt | CF$_3$CF$_2$ | — | MH$^+$= 338 t = 7.88 |
| 1.24 | —OEt | -nPr | — | Mp = 87° C. |
| 1.25 | —OEt | cyclopentyl | — | Mp = 128° C. |

Preparation of Aminothiazole Derivatives of Formula (II)

Compounds of formula (II) in which:
Y represents a fluorine atom (preparations 1.26 and 1.27),
$R_1$ and $R_2$ are in the 2-position and 5-position, respectively, with respect to the phenyl.

Preparation 1.26

4-(5-Cyclohexyl-2-methoxyphenyl)-5-fluorothiazol-2-ylamine 3.4 g of Selectfluor© are added to a solution of 2.5 g of the compound obtained in preparation 1.3 described above, in 30 ml of DMF, and the medium is stirred at AT for 2 h. The medium is hydrolysed with 2M ammonia in ethanol, concentrated, and then diluted in water. The crude is filtered, and the solid is taken up in DCM and washed with water, then with 1M sodium hydroxide and with a saturated NaCl solution. After drying of the organic phase over MgSO$_4$ and evaporation, the crude is purified by flash chromatography.

600 mg of the expected product are obtained in the form of a white powder.
Mp=159° C.

Preparation 1.27

4-(5-Propyl-2-methoxyphenyl)-5-fluorothiazol-2-ylamine

The compound is prepared according to preparation 1.26, from the compound of preparation 1.4.
Mp=107° C.
Elemental analysis: % C 59.06 (theoretical 58.63) % H 5.85 (theoretical 5.68) % N 10.22 (theoretical 10.52)

EXAMPLE 1

(Compound No. 9) N-[4-(2-methoxy-5-propylphenyl)thiazol-2-yl]-N'-4-(3-morpholin-4-ylpropyl)piperazin-1-yl]urea Compound of general formula (I) in which:
$R_1$=2-OMe; $R_2$=5-nPr; $R_3$=3-(morpholin-4-ylpropyl); a=2

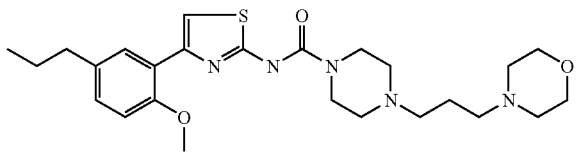

1.1. Preparation of N-[4-(2-methoxy-5-propylphenyl)thiazol-2-yl]-N'-[4-(3-morpholin-4-ylpropyl) piperazin-1-yl]urea 0.18 g of DSC is added to a solution of 0.1 g of 4-(2-(methoxy-5-propylphenyl)-1,3-thiazol-2-amine, obtained in preparation 1.4 above, in 2 ml of DMF, and the medium is stirred at AT for 12 hours. 0.05 g of 1-(morpholin-4-ylpropyl) piperazine is added and the medium is stirred at AT for 3 hours. The medium is hydrolysed with a saturated NaHCO$_3$ solution and then extracted in DCM. The organic phase is washed with water and then with a saturated NaCl solution, and then concentrated. After drying over MgSO$_4$, the solution is concentrated and purified by flash chromatography on silica gel. The solid is taken up in DCM and treated with a 2M solution of HCl in ether, and the suspension is then evaporated, to give 0.077 g of the expected compound in the form of its hydrochloride.
Mp=229° C.

EXAMPLE 2

(Compound No. 35) N-[4-(2-methoxy-5-propylphenyl)thiazol-2-yl]-N'-[4-[2-(3-ethylaminopyrrolidin-1-yl)ethyl]-[1,4]diazepan-1-yl]urea Compound of general formula (I) in which:
$R_1$=2-OCH$_3$; $R_2$=5-(CH$_2$)$_2$CH$_3$; $R_3$=4-[2-(3-ethylaminopyrrolidin-1-yl)ethyl]; a=3

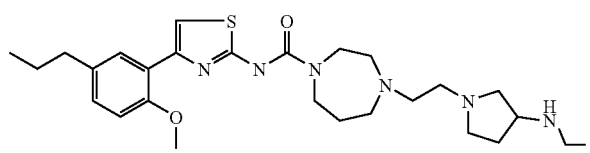

2.1 Preparation of N-[4-(2-methoxy-5-propylphenyl)thiazol-2-yl]-N'-[4-(2-chloroacetyl)-[1,4]diazepan-1-yl]urea 4 g of DSC are added to a solution of 3.87 g of 4-(2-(methoxy-5-propylphenyl)-1,3-thiazol-2-amine, obtained in preparation 1.4 above, in 60 ml of DCM, and the medium is stirred at AT for 12 hours. 5.7 g of 2-chloro-1-[1,4]diazepan-1-ylethanone and 3.26 ml of triethylamine are added. The medium is stirred at AT for 3 hours. The medium is hydrolysed with a saturated NaHCO$_3$ solution and then extracted in DCM. The organic phase is washed with water and then with brine, and then concentrated. After drying over MgSO$_4$, the solution is concentrated, to give 5.9 g of the expected compound.
MH+=452 at t=8.53 min

2.2. Preparation of N-[4-(2-methoxy-5-propylphenyl)thiazol-2-yl]-N'-[4-[2-(3-acetylaminopyrrolidin-1-yl)acetyl]-[1,4]diazepan-1-yl]urea (Compound No. 32)

Compound of general formula (I) in which:
$R_1$=2-OCH$_3$; $R_2$=5-(CH$_2$)$_2$CH$_3$; $R_3$=4-[2-(3-acetylaminopyrrolidin-1-yl)acetyl]; a=3

0.62 g of 3-acetamidopyrrolidine followed by 0.612 g of K$_2$CO$_3$ are added to a solution of 2 g of 4-(2-chloroacetyl)-[1,4]diazepane-1-carboxylic acid [4-(2-methoxy-5-propylphenyl)thiazol-2-yl]amide prepared in step 2.1, in 10 ml of acetonitrile. The medium is stirred at AT for 48 h. After filtration, the medium is washed with a 1M NaOH solution and then with water and with a saturated NaCl solution. After drying over MgSO$_4$, the solution is concentrated and then purified by flash chromatography, to give 0.95 g of the expected product.
EA: % C=56.94 % H=6.89 % N=14.52 (2H$_2$O)
MH+=543 at t=5.85 min.

2.3. Preparation of N-[4-(2-methoxy-5-propylphenyl)thiazol-2-yl]-N'-[4-[2-(3-ethylaminopyrrolidin-1-yl)ethyl]-[1,4]diazepan-1-yl]urea 2.2 ml of a 65% solution of Red-al in toluene are added, at 0° C., to a solution of 0.79 g of 4-[2-(3-acetylaminopyrrolidin-1-yl)acetyl]-[1,4]-diazepane-1-carboxylic acid [4-(2-methoxy-5-propylphenyl)thiazol-2-yl]amide prepared in step 2.2, in 3 ml of DCM. After stirring at AT for 3 hours, the medium is concentrated and then taken up in DCM and washed with 1M sodium hydroxide, with water, and then with a saturated NaCl solution. After drying over MgSO$_4$, the organic phase is concentrated and then purified by flash chromatography, to give 0.27 g of the expected product.
MH+=515 at t=8.77 min.

EXAMPLE 3

(Compound No. 76) (R)—N-[4-(5-cyclohexyl-2-methoxyphenyl)thiazol-2-yl]-N'-[4-(1-methylpiperidin-3-ylmethyl)piperazin-1-yl]urea Compound of formula (I) in which:
$R_1$=2-OCH$_3$; $R_2$=5-CyHex; $R_3$=(R)-4-(1-methylpiperidin-3-ylmethyl); a=2

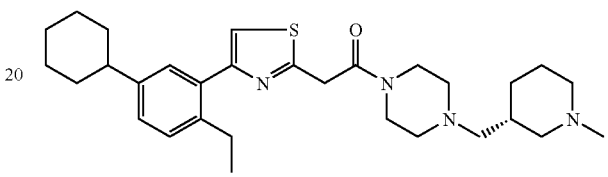

3.1. Preparation of (R)-3-methanesulphonyloxymethylpiperidine-1-carboxylic acid tert-butyl ester 2.16 ml of methanesulphonyl chloride followed by 3.86 ml of triethylamine are added to a solution of 5 g of (R)-3-hydroxymethylpiperidine-1-carboxylic acid tert-butyl ester in 80 ml of DCM cooled to 0° C. The medium is stirred at 0° C. for 1 h 30 min and 0.7 ml of triethylamine and 0.54 ml of methanesulphonyl chloride are again added. After 30 min at 0° C., the medium is hydrolysed, and the organic phase is washed twice in water and then with a saturated NaCl solution, and then dried over MgSO$_4$. The medium is evaporated, to give 6.8 g of a pale yellow oil.

3.2. Preparation of (R)-3-(4-benzylpiperazin-1-ylmethyl)piperidine-1-carboxylic acid tert-butyl ester The crude obtained in step 3.1 is dissolved in 75 ml of toluene. 12.16 g of benzylpiperazine are added, and the reaction medium is sealed and then heated at 150° C. for 5 hours. After a return to AT, the medium is diluted in an ether/pentane mixture (1/1), and washed twice with a saturated NaHCO$_3$ solution, twice in water, and then with a saturated NaCl solution. After drying over MgSO$_4$ and evaporation, the crude is purified by flash chromatography on silica gel, to give 5.73 g of the expected solid.
MH+=374 at t=5.26 min

3.3. Preparation of (R)-1-benzyl-4-(1-methylpiperidin-3-ylmethyl)piperazine 5 g of the compound obtained in step 3.2 dissolved in 45 ml of THF are added to a solution of 1 g of LiAlH$_4$ in 45 ml of THF cooled to 0° C. The medium is stirred at AT for two hours and then cooled to 0° C. 0.96 ml of water and then 3 ml of 5M NaOH are added, the medium is then filtered, and the solid is rinsed with ether. The filtrate is evaporated, taken up in ether, and washed twice with a saturated NaHCO$_3$ solution and then with a saturated NaCl solution. After drying over MgSO$_4$ and evaporation, 3.5 g of the desired compound are recovered.
MH+=288 at t=5.68 min

3.4. Preparation of (R)-1-(1-methylpiperidin-3-ylmethyl)piperazine

A solution of 3.46 g of the compound obtained in step 3.3, in 100 ml of methanol, is hydrogenated in the presence of 1.9 g of wet 10% Pd/C under 800 kPa of hydrogen pressure at 40° C. for 3 hours. The medium is filtered and then evaporated, to give 2.26 g of a colourless oil.

3.5. Preparation of (R)—N-[4-(5-cyclohexyl-2-methoxyphenyl)thiazol-2-yl]-N'-[4-(1-methylpiperidin-3-ylmethyl)piperazin-1-yl]urea The synthesis of this compound is carried out according to the procedure described in Example 1, from 4-(5-cyclohexyl-2-methoxyphenyl)-1,3-thiazol-2-amine described in preparation 1.3 and from the compound obtained in step 3.4.
Mp=108° C.; $[\alpha]_D^{25}=-27°$ (c=1.05; MeOH)

EXAMPLE 4

(Compound No. 70) N-[4-(5-cyclohexyl-2-methoxyphenyl)thiazol-2-yl]-N'-[4-(1-isopropylpiperidin-3-yl)piperazin-1-yl]urea Compound of formula (I) in which:
$R_1$=2-OCH$_3$; $R_2$=5-CyHex; $R_3$=4-(1-isopropylpiperidin-3-yl); a=2

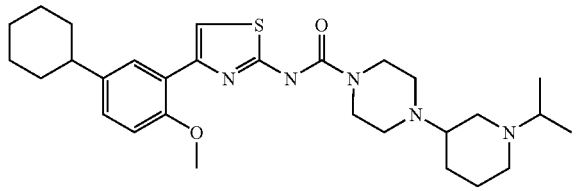

4.1. Preparation of 4-(1-benzylpiperidin-3-yl)piperazine-1-carboxylic acid tert-butyl ester 20 ml of a 10% sodium hydroxide solution are added to a suspension of 9.96 g of 1-benzyl-3-piperidone monohydrochloride hydrate in suspension in 200 ml of DCM. The medium is stirred, and the organic phase is separated by settling out and then washed with a saturated NaCl solution. After drying over MgSO$_4$, the organic phase is concentrated. The gum obtained is taken up in 180 ml of DCE, 10.1 g of Boc-piperazine and then 15.9 g of NaBH(OAc)$_3$ are added and the medium is stirred at AT for 12 h. The medium is concentrated and then taken up in EtOAc. The organic phase is washed twice with a saturated NaHCO$_3$ solution, and then with a saturated NaCl solution. After drying over MgSO$_4$, the organic phase is concentrated, to give 18.63 g of the expected product.
Mp=103° C.

4.2. Preparation of 1-(1-benzylpiperidin-3-yl)piperazine 30 g of TFA are added to a solution of 9.2 g of the compound obtained in step 4.1, in 85 ml of DCM. The medium is stirred at AT for 5 h, and then concentrated. The crude obtained is taken up in DCM and then washed 4 times with a 2M sodium hydroxide solution. The organic phase is washed with a saturated NaCl solution. After drying over MgSO$_4$, the organic phase is concentrated, to give 6.32 g of the expected product.
$^1$H NMR: δ (ppm)=7.28 (salt, 5H), 3.43 (salt, 2H), 2.88 (d, 1H), 2.70 (d, 1H), 2.64 (m, 4H), 2.43-2.22 (m, 5H), 1.85-1.58 (m, 4H), 1.39 (ddd, 1H), 1.15 (ddd, 1H).

4.3. Preparation of N-[4-(5-cyclohexyl-2-methoxyphenyl)thiazol-2-yl]-N'-[4-(1-benzylpiperidin-3-yl)piperazin-1-yl]urea (Compound No. 68)

Compound of general formula (I) in which:
$R_1$=2-OCH$_3$; $R_2$=5-CyHex; $R_3$=4-(1-benzylpiperidin-3-yl); a=2
The procedure is identical to that described in Example 1, using the 4-(5-cyclohexyl-2-methoxyphenyl)-1,3-thiazol-2-amine described in preparation 1.3 and the compound obtained in step 4.2.
Mp=90° C.

4.4. Preparation of N-[4-(5-cyclohexyl-2-methoxyphenyl)thiazol-2-yl]-N'-[4-piperidin-3-ylpiperazin-1-yl]urea (Compound No. 69)

Compound of the formula (I) in which:
$R_1$=2-OCH$_3$; $R_2$=5-CyHex; $R_3$=4-(piperidin-3-yl); a=2
1.26 g of chloroethyl chloroformate are added, at 0° C., to a solution of 1.69 g of the compound obtained in step 4.3, in 10 ml of DCE. The medium is returned to AT and is then refluxed for 45 min. The medium is evaporated and then taken up in 10 ml of MeOH and refluxed for 1 h. The crude is filtered, and the solid is rinsed with ether and dried, to give 1.27 g of the expected compound in the form of a trihydrochloride.
Mp=240° C.
MH+=484 at 6.81 min

4.5. Preparation of N-[4-(5-cyclohexyl-2-methoxyphenyl)thiazol-2-yl]-N'-[4-(1-isopropylpiperidin-3-yl)piperazin-1-yl]urea (Compound No. 70)

Compound of formula (I) in which:
$R_1$=2-OCH$_3$; $R_2$=5-CyHex; $R_3$=4-(1-isopropylpiperidin-3-yl); a=2
0.05 ml of acetone followed by 0.15 g of NaBH(OAc)$_3$ are added to a solution of 0.2 g of the compound obtained in step 4.4, in 1.2 ml of DCE, and the medium is stirred at AT for 3 h. 0.1 ml of Et$_3$N and then 0.1 mg of NaBH(OAc)$_3$ are added. The medium is stirred at AT for 12 h. The medium is concentrated and then taken up in EtOAc. The organic phase is washed twice with a saturated NaHCO$_3$ solution, and then with a saturated NaCl solution. After drying over MgSO$_4$, the organic phase is concentrated and then purified by flash chromatography to give 0.11 g of the expected product.
Mp=130° C.
MH+=526 at t=7.06 min

EXAMPLE 5

(Compound No. 74) N-[4-(5-cyclohexyl-2-methoxyphenyl)thiazol-2-yl]-N'-[4-(1-methylpiperidine-2-carbonyl)piperazin-1-yl]urea Compound of formula (I) in which:
$R_1$=2-OCH$_3$; $R_2$=5-CyHex; $R_3$=4-(1-methylpiperidine-2-carbonyl); a=2

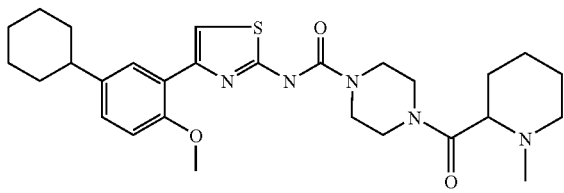

5.1. Preparation of 4-(1-benzyloxycarbonylpiperidine-2-carbonyl)piperazine-1-carboxylic acid tert-butyl ester 26.6 g of BOP, 13.6 g of 1-(carbobenzyloxy)-2-piperidinecarboxylic acid and then 11.9 ml of triethylamine are added, at 0° C., to a solution of 8 g of 1-Boc-piperazine in 80 ml of acetonitrile. The medium is stirred at AT for 12 hours and then concentrated. The medium is taken up in EtOAc, and washed three times with a saturated $Na_2CO_3$ solution and then with a saturated NaCl solution. After drying over $MgSO_4$ and evaporation, 35.45 g of reaction crude are recovered. It is taken up in DCM and then washed twice with 5M sodium hydroxide, and with a saturated NaCl solution, and then dried over $MgSO_4$. After evaporation, the solid is triturated in TBME, filtered, rinsed with TBME, and then dried, to give 17.93 g of the desired compound.
Mp=102° C.

5.2. Preparation of 4-(piperidine-2-carbonyl)piperazine-1-carboxylic acid tert-butyl ester 3.9 ml of cyclohexadiene and then 1.3 g of 10% Pd/C with a 50% water content are added, under an inert atmosphere, to a solution of 1.79 g of the compound obtained in step 5.1, in 14 ml of EtOH. The medium is stirred at AT for 24 hours and then filtered. The filtrate is evaporated, to give 1.02 g of the desired compound.

5.3. Preparation of 4-(1-methylpiperidine-2-carbonyl)piperazine-1-carboxylic acid tert-butyl ester 0.54 ml of 37% aqueous formaldehyde and then 1.41 g of $NaBH(OAc)_3$ are added to a solution of 0.99 g of the compound obtained in step 5.2, in 11 ml of DCE, and the medium is stirred at AT for 12 h. The medium is diluted in DCM and filtered through cotton wool. The organic phase is washed twice with a saturated $NaHCO_3$ solution, and then with a saturated NaCl solution. After drying over $MgSO_4$ and evaporation of the solvents, 0.84 g of the expected product is recovered.

5.4. Preparation of (1-methylpiperidin-2-yl)piperazin-1-ylmethanone 2 ml of TFA are added to a solution of 0.84 g of the compound obtained in step 5.3, in 2 ml of DCM. The medium is stirred at AT for 6 h. The medium is evaporated, taken up several times in DCM, and evaporated so as to entrain the TFA. The medium is taken up in DCM and then treated with a 10% $NH_4OH$ solution. The organic phase is dried over $MgSO_4$ and then evaporated, to give 0.15 g of the expected product.

5.5. Preparation of N-[4-(5-cyclohexyl-2-methoxyphenyl)thiazol-2-yl]-N'-[4-(1-methylpiperidine-2-carbonyl)piperazin-1-yl]urea The procedure is identical to that described in Example 1, using the 4-(5-cyclohexyl-2-methoxyphenyl)-1,3-thiazol-2-amine described in preparation 1.3 and the product obtained in step 5.4.
Mp=135° C.

EXAMPLE 6

(Compound No. 88) N-[4-(5-cyclohexyl-2-methoxyphenyl)thiazol-2-yl]-N'-[4-(1-methylpiperidin-2-ylmethyl)piperazin-1-yl]urea Compound of formula (I) in which:
$R_1$=2-$OCH_3$; $R_2$=5-CyHex; $R_3$=4-(1-methylpiperidin-2-ylmethyl); a=2

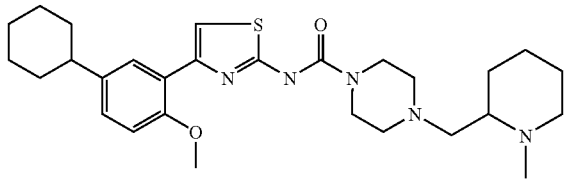

6.1. Preparation of 4-(1-benzyloxycarbonylpiperidin-2-ylmethyl)piperazine-1-carboxylic acid tert-butyl ester 162 ml of a molar solution of borane in THF are added, at 0° C., to a solution of 14 g of the compound prepared in step 5.1, in 50 ml of THF, over a period of 30 min. The medium is stirred at AT for 24 hours and then hydrolysed by the addition of water at 0° C. After dilution in EtOAc, the medium is washed three times with a saturated $Na_2CO_3$ solution, and then with a saturated NaCl solution. After drying over $MgSO_4$ and evaporation, 12.6 g of the expected compound are recovered.

6.2. Preparation of 4-piperidin-2-ylmethylpiperazine-1-carboxylic acid tert-butyl ester 14.5 ml of cyclohexadiene followed by 3.3 g of 10% Pd/C having a 50% water content are added, under an inert atmosphere, to a solution of 6.43 g of the compound obtained in step 6.1, in 50 ml of EtOH. The medium is stirred at AT for 48 hours and then filtered. The filtrate is evaporated, to give 3.63 g of the desired compound.

6.3. Preparation of 4-(1-methylpiperidin-2-ylmethyl)piperazine-1-carboxylic acid tert-butyl ester 1.91 ml of 37% aqueous formaldehyde and a few beads of 4 Å molecular sieve, followed by 5 g of $NaBH(OAc)_3$, are added to a solution of 3.34 g of the compound prepared in step 6.2, in 40 ml of DCE, and the medium is stirred at AT for 48 h. The medium is diluted in DCM, and filtered through cotton wool. The organic phase is washed twice with a saturated $NaHCO_3$ solution, and then with a saturated NaCl solution. After drying over $MgSO_4$ and evaporation of the solvents, 3.28 g of the expected product are recovered.

6.4. Preparation of 1-(1-methylpiperidin-2-ylmethyl)-piperazine 1 ml of a 4M solution of HCl in dioxane is added to a solution of 3.28 g of the compound obtained in step 6.3, in 1 ml of dioxane. The medium is stirred at AT for 48 h. The medium is filtered, and the solid is rinsed with ether and then dried, to give 2.9 g of the desired compound.

6.5. Preparation of N-[4-(5-cyclohexyl-2-methoxyphenyl)thiazol-2-yl]-N'-[4-(1-methylpiperidin-2-ylmethyl)piperazin-1-yl]urea The procedure is identical to that described in Example 1, using the 4-(5-cyclohexyl-2-methoxyphenyl)-1,3-thiazol-2-amine described in preparation 1.3 and the compound obtained in step 6.4.

Mp=103° C.

TABLE II

| No. | $R_1$ | $R_2$ | $R_3$ | Y | a | Salt | Mp(° C) M |
|---|---|---|---|---|---|---|---|
| 1 | —OCH$_3$ | —O(CH$_2$)$_2$CH$_3$ | ethyl-morpholine | H | 2 | — | 144° C. |
| 2 | —OCH$_3$ | —O(CH$_2$)$_2$CH$_3$ | propanoyl-morpholine | H | 2 | — | 96° C. |
| 3 | —OCH$_3$ | —(CH$_2$)$_2$CH$_3$ | ethyl-morpholine | H | 2 | — | 66° C. |
| 4 | —OCH$_3$ | —(CH$_2$)$_2$CH$_3$ | propanoyl-morpholine | H | 2 | — | 90° C. |
| 5 | —OCH$_3$ | cyclopentylmethyl | ethyl-morpholine | H | 2 | — | 66° C. |
| 6 | —OCH$_3$ | —(CH$_2$)$_3$CH$_3$ | propanoyl-morpholine | H | 2 | — | 133° C. |
| 7 | —OCH$_3$ | —(CH$_2$)$_3$CH$_3$ | ethyl-morpholine | H | 2 | — | 45° C. |
| 8 | —OCH$_3$ | cyclopentylmethyl | propanoyl-morpholine | H | 2 | — | 113° C. |

TABLE II-continued
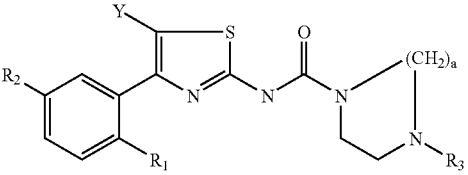
| | | | | | | | |
|---|---|---|---|---|---|---|---|
| 9 | —OCH₃ | —(CH₂)₂CH₃ | 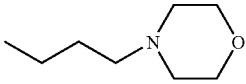 | H | 2 | HCl | 229° C. |
| 10 | —OCH₃ | —(CH₂)₂CH₃ | 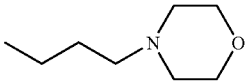 | H | 3 | HCl | 234° C. |
| 11 | —OCH₃ | —(CH₂)₂CH₃ | 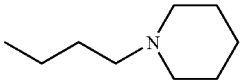 | H | 2 | HCl | 202° C. |
| 12 | —OCH₃ | —(CH₂)₂CH₃ | 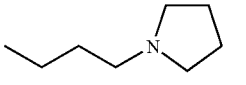 | H | 2 | HCl | 199° C. |
| 13 | —OCH₃ | —(CH₂)₂CH₃ | 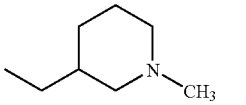 | H | 2 | HCl | 230° C. |
| 14 | —OCH₃ | —(CH₂)₂CH₃ | 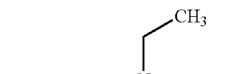 | H | 2 | HCl | 145° C. |
| 15 | —OCH₃ | —(CH₂)₂CH₃ | 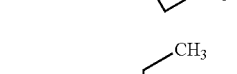 | H | 2 | HCl | 245° C. |
| 16 | —OCH₃ | —(CH₂)₂CH₃ | 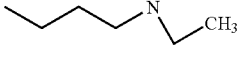 | H | 2 | HCl | 239° C. |
| 17 | —OCH₃ | —(CH₂)₂CH₃ | 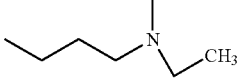 | H | 3 | HCl | 223° C. |
| 18 | —OCH₃ | —(CH₂)₂CH₃ | 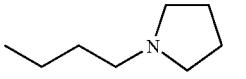 | H | 2 | HCl | 180° C. |
| 19 | —OCH₃ | —(CH₂)₂CH₃ | 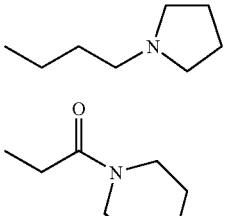 | H | 2 | HCl | 180° C. |
| 20 | —OCH₃ | —(CH₂)₂CH₃ | 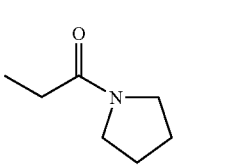 | H | 2 | HCl | 181° C. |

TABLE II-continued
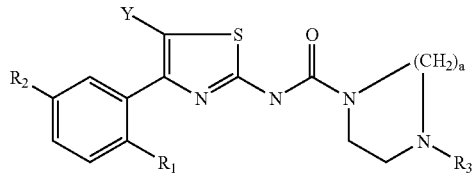
| | R₂ | R₁ | Y | | | | |
|---|---|---|---|---|---|---|---|
| 21 | —OCH₃ | —(CH₂)₂CH₃ | 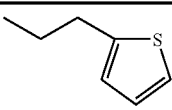 | H | 2 | HCl | 209° C. |
| 22 | —OCH₃ | —(CH₂)₂CH₃ | 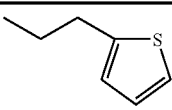 | H | 2 | HCl | 200° C. |
| 23 | —OCH₃ | —(CH₂)₂CH₃ | 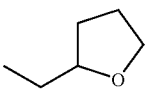 | H | 2 | HCl | 242° C. |
| 24 | —OCH₃ | —(CH₂)₂CH₃ | 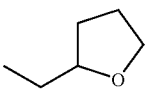 | H | 2 | HCl | 248° C. |
| 25 | —OCH₃ | 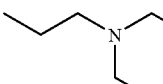 | 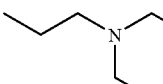 | H | 2 | — | 114° C. |
| 26 | —OCH₃ | —(CH₂)₃CH₃ | 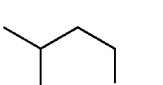 | H | 2 | — | 65° C. |
| 27 | —OCH₃ | —O(CH₂)₂CH₃ | 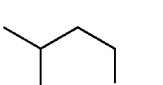 | H | 2 | — | 70° C. |
| 28 | —OCH₃ | —(CH₂)₂CH₃ | 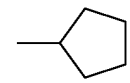 | H | 2 | — | 82° C. |
| 29 | —OCH₃ | 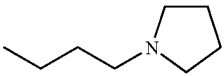 | 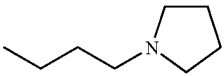 | H | 2 | HCl | MH+ = 534 at 6.14 min |
| 30 | —OCH₃ |  |  | H | 2 | — | MH+ = 498 at 6.52 min |
| 31 | —OCH₃ | —(CH₂)₂CH₃ |  | H | 2 | — | 89° C. |
| 32 | —OCH₃ | —(CH₂)₂CH₃ |  | H | 3 | — | MH+ = 543 at 5.85 min |

TABLE II-continued

| # | R2 | R1 | (cyclic amine group) | Y | a | salt | data |
|---|---|---|---|---|---|---|---|
| 33 | —OCH₃ | —(CH₂)₂CH₃ | 1-propyl-3-(ethylamino)pyrrolidine | H | 2 | — | MH+ = 501 at 5.03 min |
| 34 | —OCH₃ | —(CH₂)₂CH₃ | 1-(2-oxoethyl)pyrrolidine | H | 3 | — | MH+ = 486 at 6.04 min |
| 35 | —OCH₃ | —(CH₂)₂CH₃ | 1-propyl-3-(ethylamino)pyrrolidine | H | 3 | HCl | MH+ = 515 at 8.77 min |
| 36 | —OCH₃ | —(CH₂)₂CH₃ | 1-butylpyrrolidine | F | 2 | — | 63° C. |
| 37 | —OCH₃ | —(CH₂)₂CH₃ | 1-benzyl-3-methylpyrrolidine | H | 2 | — | 63° C. |
| 38 | —OCH₃ | —(CH₂)₅CH₃ | 1-butylpyrrolidine | H | 2 | HCl | MH+ = 500 at 6.99 min |
| 39 | —OCH₂CH₃ | —CH₂CH₃ | 1-propylpyrrolidine | H | 2 | — | 96° C. |
| 40 | —OCH₂CH₃ | —(CH₂)₃CH₃ | 1-propylpyrrolidine | H | 2 | — | 130° C. |
| 41 | —OCH₂CH₃ | cyclohexyl | 1-propylpyrrolidine | H | 2 | — | 89° C. |
| 42 | —OCH₃ | —CH₂CH₃ | 1-propylpyrrolidine | H | 2 | — | 100° C. |
| 43 | —OCH₃ | cyclohexyl | 1-methyl-3-ethylpiperidine | H | 2 | — | 106° C. |
| 44 | —OCH₃ | cyclopentyl | 1-methyl-3-ethylpiperidine | H | 2 | — | 98° C. |
| 45 | —OCH₃ | —(CH₂)₃CH₃ | 1-methyl-3-ethylpiperidine | H | 2 | — | 90° C. |

TABLE II-continued

| | R2 | (structure) | (structure) | Y | a | | mp |
|---|---|---|---|---|---|---|---|
| 46 | —OCH₃ | —(CH₂)₃CH₃ | 4-methylpiperidine-N-CH₃ | H | 2 | — | 69° C. |
| 47 | —OCH₃ | cyclohexyl- | 4-methylpiperidine-N-CH₃ | H | 2 | — | 103° C. |
| 48 | —OCH₃ | cyclopentyl- | 4-methylpiperidine-N-CH₃ | H | 2 | — | 98° C. |
| 49 | —OCH₂CH₃ | cyclohexyl- | 3-ethylpiperidine-N-CH₃ | H | 2 | — | 109° C. |
| 50 | —OCH₂CH₃ | cyclopentyl- | 3-ethylpiperidine-N-CH₃ | H | 2 | — | 108° C. |
| 51 | —OCH₂CH₃ | cyclohexyl- | 4-methylpiperidine-N-CH₃ | H | 2 | — | 106° C. |
| 52 | —OCH₂CH₃ | cyclopentyl- | 4-methylpiperidine-N-CH₃ | H | 2 | — | 96° C. |
| 53 | —OCH₂CH₃ | cyclopentyl- | propyl-pyrrolidine | H | 2 | — | 75° C. |
| 54 | —OCH₂CH₃ | —(CH₂)₃CH₃ | 4-methylpiperidine-N-CH₃ | H | 2 | — | 140° C. |
| 55 | —OCH₃ | cyclopentyl- | 4-ethylpiperidine-N-CH₃ | H | 2 | — | 102° C. |
| 56 | —OCH₂CH₃ | —(CH₂)₃CH₃ | 3-ethylpiperidine-N-CH₃ | H | 2 | — | 91° C. |
| 57 | —OCH₂CH₃ | cyclohexyl- | 4-ethylpiperidine-N-CH₃ | H | 2 | — | 110° C. |

TABLE II-continued

| # | R2 | (aryl group) | (amine group) | Y | a | salt | mp/MS |
|---|---|---|---|---|---|---|---|
| 58 | —OCH₃ | cyclohexyl-CH₂— | propyl-pyrrolidine | F | 2 | HCl | MH+ = 516 at 6.79 min |
| 59 | —OCH₃ | cyclohexyl-CH₂— | (1-methylpiperidin-4-yl)methyl | F | 2 | HCl | MH+ = 515 at 6.01 min |
| 60 | —OCH₃ | cyclohexyl-CH₂— | propyl-morpholine | F | 2 | HCl | MH+ = 532 at 6.91 min |
| 61 | —OCH₃ | cyclohexyl-CH₂— | (1-methylpiperidin-4-yl)methyl | H | 2 | — | 118° C. |
| 62 | —OCH₃ | —(CH₂)₃CH₃ | (1-methylpiperidin-4-yl)methyl | H | 2 | — | 84° C. |
| 63 | —OCH₃ | cyclopentyl-CH₂— | 1-benzyl-3-methylpiperidine | H | 2 | — | 79° C. |
| 64 | —OCH₃ | CF₃CF₂— | (1-methylpiperidin-4-yl)methyl | H | 2 | — | 97° C. |
| 65 | —OCH₃ | CF₃CF₂— | 1,4-dimethylpiperidine | H | 2 | — | 172° C. |
| 66 | —OCH₃ | cyclohexyl-CH₂— | 1,3-dimethylpiperidine | H | 2 | — | 107° C. |
| 67 | —OCH₃ | cyclopentyl-CH₂— | 3-methylpiperidine | H | 2 | — | 83° C. |
| 68 | —OCH₃ | cyclohexyl-CH₂— | 1-benzyl-3-methylpiperidine | H | 2 | — | 90° C. |
| 69 | —OCH₃ | cyclohexyl-CH₂— | 3-methylpiperidine | H | 2 | 3 HCl | 240° C. |

TABLE II-continued
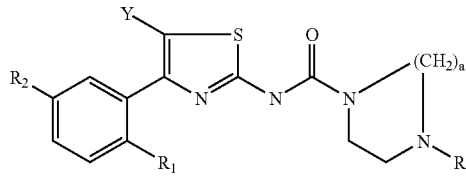
| 70 | —OCH₃ | 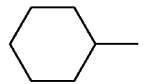 | 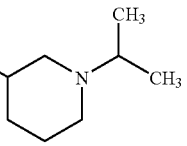 | H | 2 | — | 130° C. |
|---|---|---|---|---|---|---|---|
| 71 | —OCH₃ | 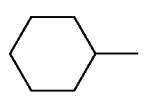 | 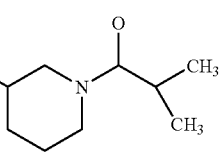 | H | 2 | — | 127° C. |
| 72 | —OCH₃ | 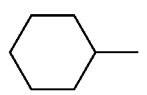 | 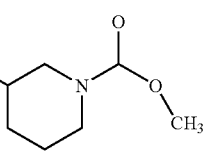 | H | 2 | — | 125° C. |
| 73 | —OCH₃ | 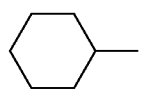 | 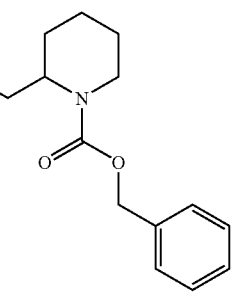 | H | 2 | — | 122° C. |
| 74 | —OCH₃ | 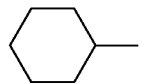 | 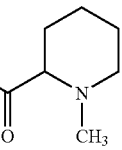 | H | 2 | — | 135° C. |
| 75 | —OCH₃ | 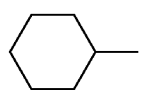 | 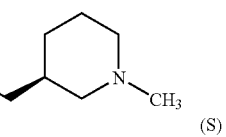 (S) | H | 2 | — | 107° C. |
| 76 | —OCH₃ | 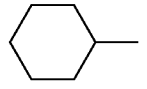 | 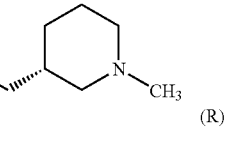 (R) | H | 2 | — | 108° C. |
| 77 | —OCH₃ | —(CH₂)₃CH₃ |  (R) | H | 2 | — | 85° C. |

TABLE II-continued

| | | | | Y | a | | m.p. |
|---|---|---|---|---|---|---|---|
| 78 | —OCH₃ | cyclopentylmethyl | 3-ethyl-1-methylpiperidine (R) | H | 2 | — | 94° C. |
| 79 | —OCH₃ | —(CH₂)₅CH₃ | 3-ethyl-1-methylpiperidine | H | 2 | — | 68° C. |
| 80 | —OCH₂CH₃ | —(CH₂)₅CH₃ | 3-ethyl-1-methylpiperidine | H | 2 | — | 65° C. |
| 81 | —OCH₂CH₃ | —(CH₂)₃CH₃ | 3-ethyl-1-methylpiperidine (R) | H | 2 | — | 75° C. |
| 82 | —OCH₃ | (CH₃)₂CHCH₂CH₂— | 3-ethyl-1-methylpiperidine | H | 2 | — | 85° C. |
| 83 | —OCH₂CH₃ | —(CH₂)₂CH₃ | 3-ethyl-1-methylpiperidine (R) | H | 2 | — | 74° C. |
| 84 | —OCH₂CH₃ | cyclopentylmethyl | 3-ethyl-1-methylpiperidine (R) | H | 2 | — | 92° C. |
| 85 | —O(CH₂)₂CH₃ | —CH₂CH₃ | 3-ethyl-1-methylpiperidine | H | 2 | — | 73° C. |

TABLE II-continued

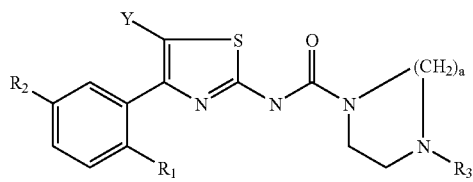

| | R2 | R1 | (NR3 group) | Y | a | | mp |
|---|---|---|---|---|---|---|---|
| 86 | —OCH₃ | —CH₂CH₃ | 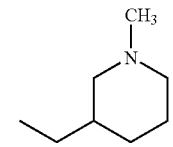 1-methyl-3-ethylpiperidine | H | 2 | — | 86° C. |
| 87 | —OCH₂CH₃ | cyclohexyl | 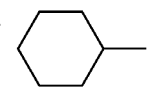 (R)-1-methyl-3-ethylpiperidine | H | 2 | — | 98° C., 103° C. |
| 88 | —OCH₃ | cyclohexyl | 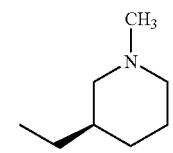 1-methyl-2-ethylpiperidine | H | 2 | — | 103° C. |
| 89 | —OCH₃ | cyclohexyl | 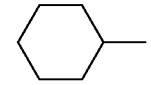 2-ethylpiperidine | H | 2 | — | 121° C. |
| 90 | —OCH₃ | cyclohexyl | 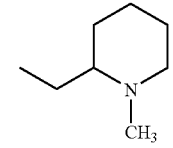 methyl 2-ethylpiperidine-1-carboxylate | H | 2 | — | 119° C. |
| 91 | —OCH₃ | —CH₃ | 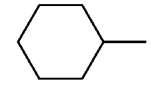 | H | 2 | — | 95° C. |
| 92 | —OCH₃ | cyclohexyl | 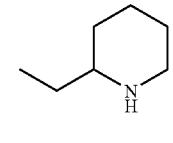 1-benzyl-3-pyrrolidine | H | 2 | — | 85° C. |
| 93 | —OCH₃ | cyclohexyl | 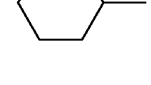 tert-butyl 3-ethylpiperidine-1-carboxylate | H | 2 | — | 125° C. |

TABLE II-continued
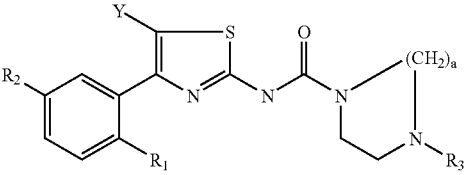
| | | | | | | |
|---|---|---|---|---|---|---|
| 94 | —OCH₃ | 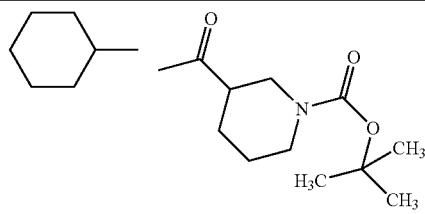 | 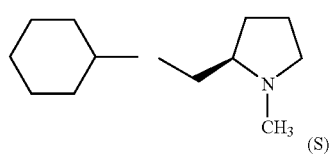 | H | 3 | — | 112° C. |
| 95 | —OCH₃ | 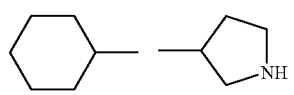 | | H | 2 | — | 101° C. |
| 96 | —OCH₃ | | 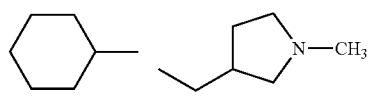 | H | 2 | — | 215° C. |
| 97 | —OCH₃ | | 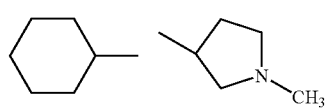 | H | 2 | — | 103° C. |
| 98 | —OCH₃ | | 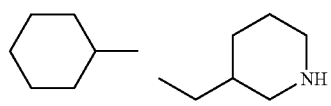 | H | 2 | — | 106° C. |
| 99 | —OCH₃ | | 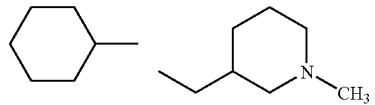 | H | 2 | — | 128° C. |
| 100 | —OCH₃ | | 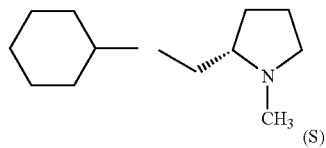 | H | 3 | — | 88° C. |
| 101 | —OCH₃ | | 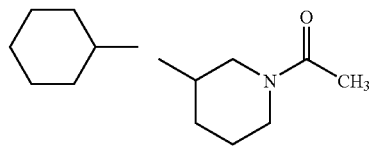 | H | 2 | — | 122° C. |
| 102 | —OCH₃ | | 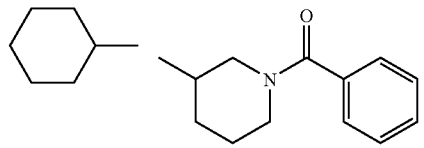 | H | 2 | — | 146° C. |
| 103 | —OCH₃ | | 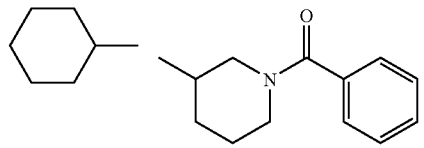 | H | 2 | — | 132° C. |

TABLE II-continued
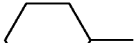
| No. | R₁ | R₂ | R₃ | Y | a | Salt | Mp (° C.) M | Other analysis |
|---|---|---|---|---|---|---|---|---|
| 104 | —OCH₃ | 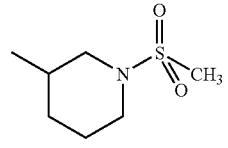 |  | H | 2 | — | 132° C. | |
| 105 | —OCH₃ | 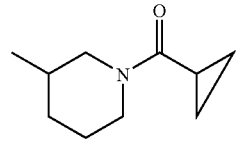 | 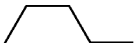 | H | 2 | — | 119° C. | — |
| 106 | —OCH₃ | 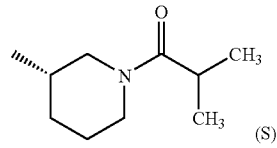 | 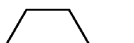 (S) | H | 2 | — | 118° C. | — |
| 107 | —OCH₃ | 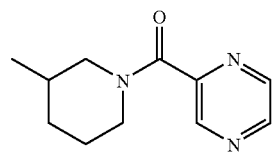 | 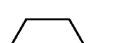 | H | 2 | — | — | MH+ = 590 at 7.52 min |
| 108 | —OCH₃ | 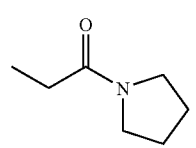 | 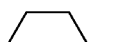 | H | 2 | — | — | C:63.17 H:7.20 N:13.51 |
| 109 | —OCH₂CH₃ | 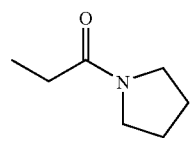 | 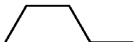 | H | 2 | — | 111° C. | — |
| 110 | —OCH₂CH₃ | | 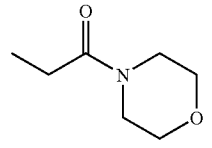 | H | 2 | — | 113° C. | — |
| 111 | —OCH₃ | 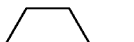 | 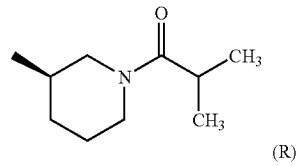 (R) | H | 2 | — | 98° C. | a_D = −6.2° c = 1.0 M MeOH |

TABLE II-continued

[Structure: R2 and R1 substituted phenyl connected to thiazole (with Y) connected via NH-C(O)-N to a piperazine-like ring with (CH2)a and N-R3]

| No. | R1 | R2 | R3 | Y | a | Salt | M |
|-----|-----|-----|-----|---|---|------|---|
| 112 | —OCH3 | cyclohexyl-CH2— | (S)-3-ethylpiperidin-1-yl sulfonylmethyl (N-SO2CH3) | H | 2 | — | 158° C. |
| 113 | —OCH3 | cyclohexyl-CH2— | (S)-3-ethylpiperidine N-C(O)-(pyridine N-oxide) | H | 2 | — | 158° C. |
| 114 | —OCH3 | cyclohexyl-CH2— | (S)-3-ethylpiperidine N-C(O)-OCH3 | H | 2 | — | 125° C. |
| 115 | —OCH3 | cyclohexyl-CH2— | (S)-3-ethylpiperidine N-C(O)CH3 | H | 2 | — | 157° C. |
| 116 | —OCH3 | cyclohexyl-CH2— | morpholine N-C(O)-CH2- | H | 2 | — | 119° C. |
| 117 | —OCH3 | cyclohexyl-CH2— | 4-methylpiperidine N-CH2-phenyl | H | 2 | — | 81° C. |
| 118 | —OCH3 | cyclohexyl-CH2— | (S)-3-ethylpiperidine N-CH2CH2F | H | 2 | — | 91° C. |
| 119 | —OCH3 | cyclohexyl-CH2— | pyrrolidine N-CH2-C(O)- | H | 2 | — | 117° C. |
| 120 | —OCH3 | cyclohexyl-CH2— | 2-ethylmorpholine N-CH2-phenyl | H | 2 | — | 78° C. |

The compounds according to the invention were subjected to pharmacological assays in order to determine their modulatory effect on the activity of chemokine receptors.

Chemokines are low molecular weight proteins that belong to the pro-inflammatory cytokine family and are involved in leukocyte and endothelial cell chemotaxis. Chemokines control many biological processes and are associated with inflammatory disorders that appear during states of stress, during injuries or during infections; modulating the effect of chemokines makes it possible to prevent or treat pathologies such as asthma, arthritis, allergies, autoimmune diseases, atherosclerosis or angiogenesis (C. D. Paavola et al., J. Biol. Chem., 1998, 273, (50), 33157-33165).

Among the chemokines, hMCP-1 (human monocyte chemotactic protein) which belongs to the CC chemokine group and which is a natural agonist of the CCR2b receptor, is distinguished.

The inhibitory activity of the compounds according to the invention on cells expressing the human CCR2b receptor was measured. The concentration of natural agonist hMCP-1 that inhibits 50% ($IC_{50}$) of the activity of the CCR2b receptor is 0.57 nM. The compounds according to the invention exhibit an $IC_{50}$ that is generally less than 0.1 µM.

For example, Compound No. 14 exhibited an $IC_{50}$ of 0.0033 µM;

Compound No. 28 exhibited an $IC_{50}$ of 0.028 µM;

Compound No. 55 exhibited an $IC_{50}$ of 0.014 µM.

The inhibition of chemotaxis was also measured on human THP-1 monocyte cells (sold by DSMZ—Germany), using a technique adapted from that described by A. Albini et al., Cancer Res., 1987, 47, 3239-3245. Under these conditions, hMCP-1 exhibits an $IC_{50}$ of 6 nM. The compounds according to the invention exhibit an $IC_{50}$ that is generally less than 1 µM.

The inhibition of chemotaxis by the compounds according to the invention is a sign of their antagonistic activity on chemokine receptors, and in particular the CCR2b receptor.

It therefore appears that the compounds according to the invention are antagonist of the effect of chemokines, in particular of hMCP-1.

The inhibitory activity of the compounds according to the invention was also measured on PBMCs (peripheral blood mononuclear cells) infected with the HIV-1 Bal virus, according to a technique adapted from that described by V. Dolle et al., J. Med. Chem., 2000, 43, 3949, 3962. According to this technique, the PBMCs are infected with HIV-1 Bal and the compounds to be tested are then added to the culture medium for 5 days. At the end of this exposure, the amount of reverse transcriptase in the supernatant is measured, which correlates with the level of viral replication in the cells.

Under these conditions, AZT, a reference molecule which inhibits viral replication, exhibits an $IC_{50}$ of less than 1 µM. Compounds according to the invention also exhibit $IC_{50}$ values of less than 1 µM. For example, Compound No. 30 showed an $IC_{50}$ of 0.6 µM.

The compounds according to the invention can therefore be used for preparing medicinal products, in particular medicinal products that are agonists of the effect of chemokines.

Thus, according to another of its aspects, a subject of the present invention is medicinal products which comprise a compound of formula (I) or an addition salt of the latter with a pharmaceutically acceptable acid, or else a hydrate or a solvate.

These medicinal products find their use in therapeutics, in particular in the prevention and treatment of various pathologies, such as:

acute and chronic immunoinflammatory diseases and syndromes, such as atherosclerosis, restenoses, chronic pulmonary diseases, in particular COPD (chronic obstructive pulmonary disease); respiratory distress syndrome; bronchial hyperactivity; colitis; silicosis; fibrous pathologies, pulmonary fibroses, cystic fibroses; viral or bacterial infections, AIDS, meningitis, malaria, leprosy, tuberculosis, herpes, cytomegalovirus infections; septic shocks, septicaemia, endotoxic shocks; transplant rejections; bone pathologies such as osteoporosis, osteoarthritis; conjunctivitis; atypical or contact dermatitis; eczema; glomerulonephritis; pancreatitis; ulcerative colitis, autoimmune diseases such as rheumatoid arthritis, multiple sclerosis, amyotrophic lateral sclerosis, Crohn's disease, lupus erythematosus, scleroderma, psoriasis; Parkinson's disease; Alzheimer's disease; diabetes; cachexia; obesity;

the treatment of pain, in particular neuropathic and inflammatory pain;

allergic diseases such as allergic respiratory diseases, asthma, rhinitis, pulmonary hypersenstitivity, delayed hypersensitivity;

diseases and disorders in which angiogenic processes are involved, such as cancers (intratumoral angiogenesis), retinal diseases (age-related macular degeneration: ARMD);

cardiac pathologies: haemodynamic shock; cardiac ischaemias; post-ischaemic reperfusion attacks; myocardial infarction, coronary thrombosis, heart failure, angina pectoris.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, or a hydrate or solvate of said compound, and also at least one pharmaceutically acceptable excipient.

Said excipients are chosen, according to the pharmaceutical form and the method of administration desired, from the usual excipients that are known to those skilled in the art.

In the pharmaceutical compositions of the present invention for oral, sublingual, subcutaneous, intamuscular, intravenous, topical, local, intratracheal, intranasal, transdermal or rectal administration, the active principle of formula (I) above, or its possible salt, solvate or hydrate, can be administered in unit administration form, as a mixture with conventional pharmaceutical excipients, to animals and to human beings for the prophylaxis or the treatment of the disorders or of the diseases above.

The suitable unit administration forms comprise oral forms such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in the form of a tablet can comprise the following constituents:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

When given orally, the dose of active principle administered per day can reach 0.1 to 1000 mg/kg, taken in one or more doses.

There may be specific cases where higher or lower dosages are appropriate; such dosages do not depart from the context of the invention. According to the usual practice, the dosage appropriate for each patient is determined by the physician according to the method of administration, and the weight and response of said patient.

According to another of its aspects, the present invention also relates to a method of treating the pathologies indicated above, which comprises the administration of an effective dose of a compound according to the invention, or one of its pharmaceutically acceptable salts or hydrates or solvates, to a patient.

What is claimed is:

1. A compound of formula (I):

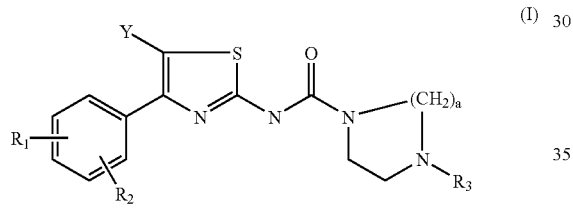

wherein $R_1$ is selected from the group consisting of halogen, $(C_1\text{-}C_8)$alkyl, trifluoro$(C_1\text{-}C_4)$alkyl, —OH, —O—$(C_1\text{-}C_8)$alkyl, —O-trifluoro$(C_1\text{-}C_8)$alkyl, —O—$(C_3\text{-}C_{10})$cycloalkyl$(C_1\text{-}C_8)$alkyl, —O—$(C_3\text{-}C_{10})$cycloalkyl, —O—CH$_2$—CH=CH$_2$ and $(C_1\text{-}C_4)$alkylthio;

$R_2$ is selected from the group consisting of halogen, —OH, $(C_1\text{-}C_8)$alkyl, trifluoro$(C_1\text{-}C_4)$alkyl, perfluoro$(C_1\text{-}C_4)$alkyl, $(C_3\text{-}C_{10})$cycloalkyl, —O—$(C_1\text{-}C_8)$alkyl, —O—$(C_3\text{-}C_{10})$— cycloalkyl$(C_1\text{-}C_8)$alkyl, —O—$(C_3\text{-}C_{10})$cycloalkyl, —O—CH$_2$—CH=CH$_2$ and $(C_3\text{-}C_8)$cycloalkyl$(C_1\text{-}C_8)$alkyl;

Y represents a hydrogen atom or a halogen;

$R_3$ represents:

a1) a group of formula —(CH$_2$)$_p$-A in which p represents 0, 1, 2, 3 or 4, and:

when p represents 2, 3 or 4, A represents a group of formula:

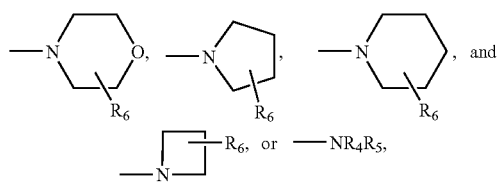

in which $R_6$ is selected from the group consisting of H, F, $(C_1\text{-}C_4)$alkyl, —(CH$_2$)OH, —(CH$_2$)$_n$O$(C_1\text{-}C_4)$alkyl and —(CH$_2$)$_n$NR$_4$R$_5$, where n represents 0, 1 or 2, and $R_4$ and $R_5$ represent, independently of one another, a hydrogen atom, or a $(C_1\text{-}C_8)$alkyl, —CO$(C_1\text{-}C_4)$alkyl or —CO—O—$(C_1\text{-}C_8)$alkyl group;

or, when p represents 1, 2, 3 or 4, A represents a group of formula:

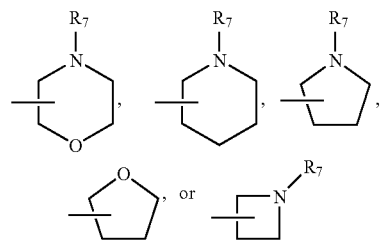

in which $R_7$ is selected from the group consisting of H, $(C_1\text{-}C_8)$alkyl, —CO—$(C_1\text{-}C_8)$alkyl, benzyl, —CO—O—$(C_1\text{-}C_8)$alkyl, —CO—O-benzyl, —CO-phenyl, —CO-hetero aryl, —CO—$(C_3\text{-}C_{10})$-cycloalkyl, —SO$_2$—$(C_1\text{-}C_8)$alkyl, —SO$_2$—$(C_3\text{-}C_8)$cycloalkyl and —SO$_2$-heteroaryl;

or, when p represents 0, 1, 2, 3 or 4, A represents a group of formula:

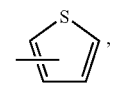

said group being optionally substituted with a $(C_1\text{-}C_4)$alkyl group;

a2) a group of formula —(CH$_2$)$_p$—CO-A in which p represents 1, 2, 3 or 4,

A represents a group of formula:

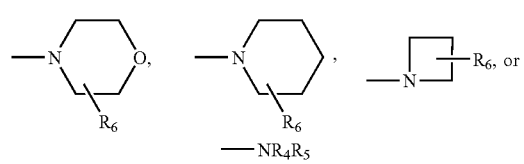

in which $R_4$, $R_5$ and $R_6$ are as defined above; or a3) a group of formula —CO(CH$_2$)$_p$-A in which p represents 0, 1, 2, 3 or 4 when p represents 1, 2, 3 or 4, A represents a group of formula:

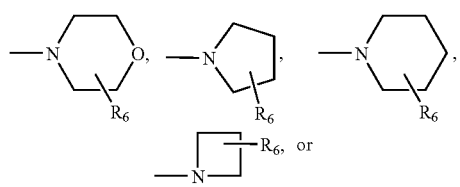

—NR$_4$R$_5$, in which $R_4$, $R_5$ and $R_6$ are as defined above;

or, when p represents 0, 1, 2, 3 or 4, A represents a group of formula:

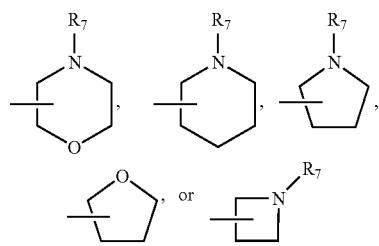

in which R$_7$ is as defined above;

or, when p represents 0, 1, 2, 3 or 4, A represents a group of formula:

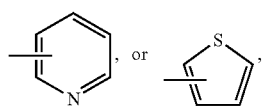

said group being optionally substituted with a (C$_1$-C$_4$)alkyl group;

a represents 2 or 3;

or an acid addition salt thereof.

2. A compound according to claim 1, of formula (I.a):

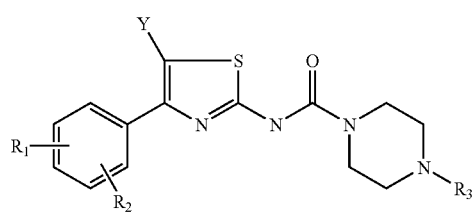

wherein:

R$_1$, R$_2$, R$_3$ and Y are as defined in claim 1, or an acid addition salt thereof.

3. A compound according to claim 1, of formula (I.b):

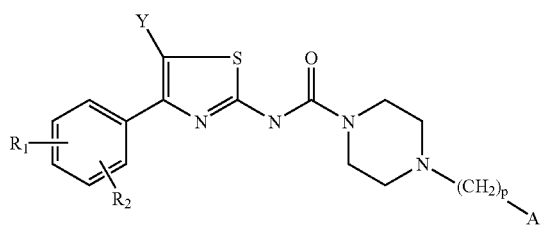

in which R$_1$, R$_2$, Y, p and A are as defined in claim 1, or an acid addition salt thereof.

4. A compound according to claim 1, wherein R$_1$ represents a —O—(C$_1$-C$_8$)alkyl group.

5. A compound according to claim 1, wherein R$_2$ represents a (C$_1$-C$_8$)alkyl, (C$_3$-C$_{10}$)cycloalkyl, perfluoro(C$_1$-C$_4$)alkyl or —O—(C$_1$-C$_8$)alkyl group.

6. A compound according to claim 1 selected from the group consisting of:

(R)—N-[4-(5-cyclohexyl-2-methoxyphenyl)thiazol-2-yl]-N'-[4-(1-methylpiperidin-3-ylmethyl)piperazin-1-yl]urea, N-[4-(2-methoxy-5-propoxyphenyl)thiazol-2-yl]-N'-[4-(2-morpholin-4-ylethyl)piperazin-1-yl]urea, N-[4-(2-methoxy-5-propylphenyl)thiazol-2-yl]-N'-[4-(3-piperidin-1-ylpropyl)piperazin-1-yl]urea, N-[4-(2-methoxy-5-propylphenyl)thiazol-2-yl]-N'-[4-(2-dimethylaminoethyl)piperazin-1-yl]urea, N-[4-(2-methoxy-5-propylphenyl)thiazol-2-yl]-N'-[4-(2-thiophen-2-ylethyl)piperazin-1-yl]urea, N-[4-(2-methoxy-5-propylphenyl)thiazol-2-yl]-N'-[4-[2-(tetrahydrofuran-2-yl)ethyl]piperazin-1-yl]urea, N-[4-(2-methoxy-5-propylphenyl)thiazol-2-yl]-N'-[4-[2-(3-ethylaminopyrrolidin-1-yl)ethyl]piperazin-1-yl]urea, N-[4-(2-methoxy-5-pentafluoroethylphenyl)thiazol-2-yl]-N'-[4-(2-pyrrolidin-1-ylethyl)piperazin-1-yl]urea, N-[4-(5-cyclohexyl-2-methoxyphenyl)thiazol-2-yl]-N'-[4-(2-pyrrolidin-1-ylethyl)piperazin-1-yl]urea, N-[4-(5-cyclohexyl-2-methoxyphenyl)thiazol-2-yl]-N'-[4-(2-oxo-2-morpholino-4-ylethyl)piperazin-1-yl]urea, N-[4-(5-cyclohexyl-2-ethoxyphenyl)thiazol-2-yl]-N'-[4-(2-oxo-2-morpholino-4-ylethyl)piperazin-1-yl]urea, (S)N-[4-(5-cyclohexyl-2-methoxyphenyl)thiazol-2-yl]-N'-[4-(1-sulphomethylpiperidin-3-ylmethyl)piperazin-1-yl]urea, and N-[4-(5-cyclohexyl-2-methoxyphenyl)thiazol-2-yl]-N'-[4-(1-oxo-1-(1-oxopyridin-2-yl)meth-1-ylpiperidin-3-ylmethyl)piperazin-1-yl]urea;

or an acid addition salt thereof.

7. A pharmaceutical composition comprising a compound of formula (I) according to claim 1, or a pharmaceutically acceptable salt thereof; and at least one pharmaceutically acceptable excipient.

8. A pharmaceutical composition comprising a compound according to claim 6, or a pharmaceutically acceptable salt thereof; and at least one pharmaceutically acceptable excipient.

9. The compound according to claim 1, selected from the group consisting of:

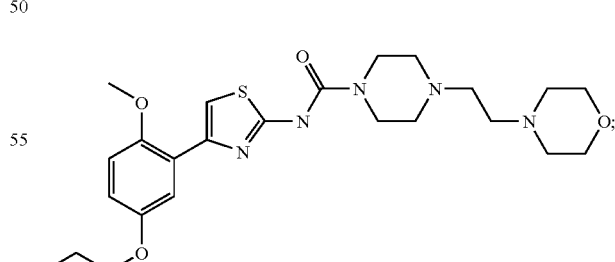

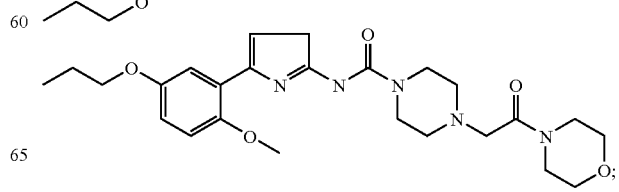

-continued
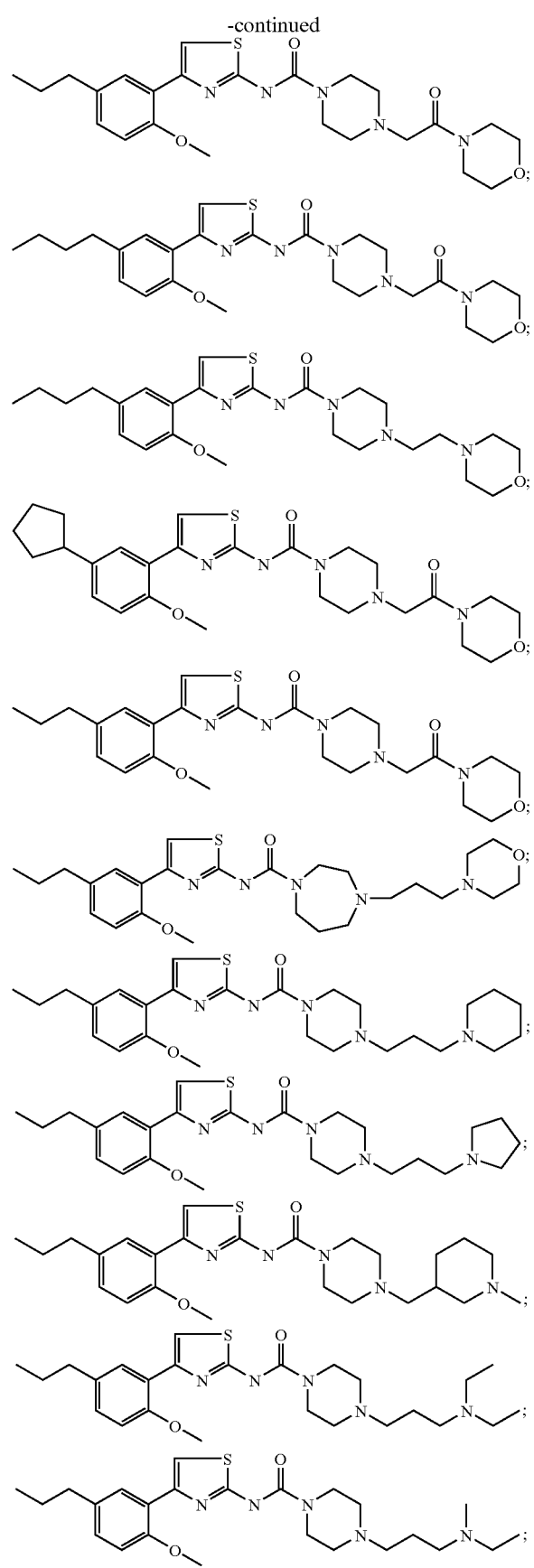
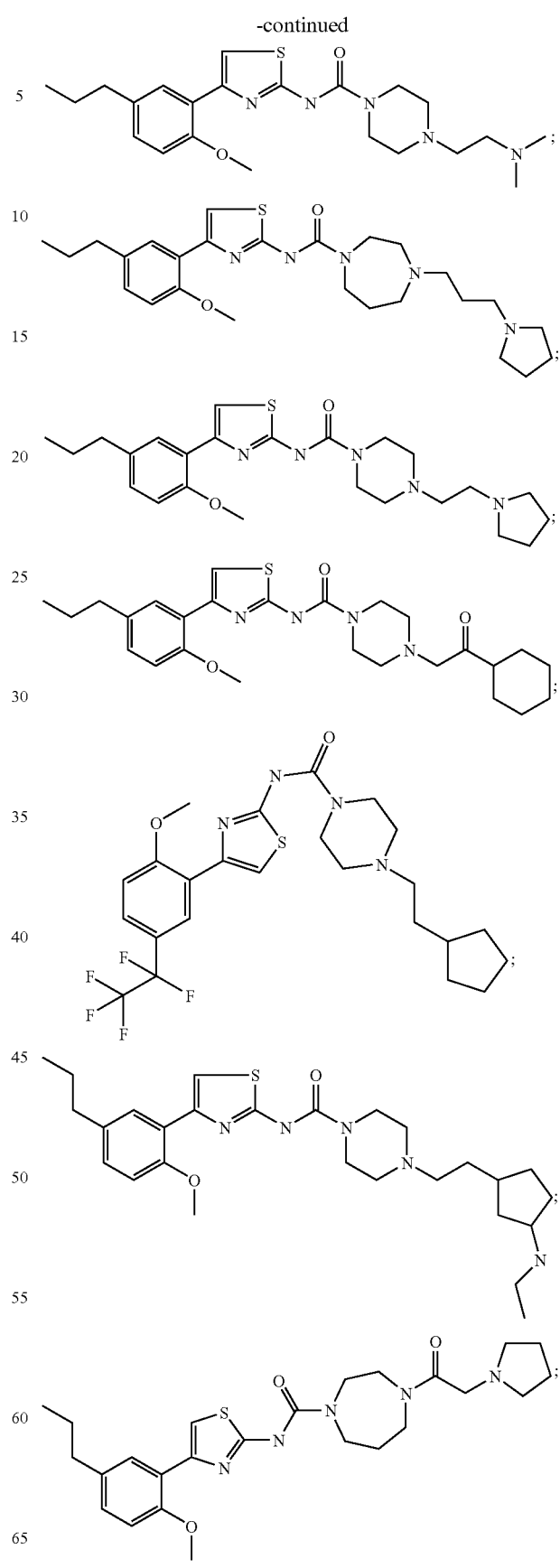

-continued
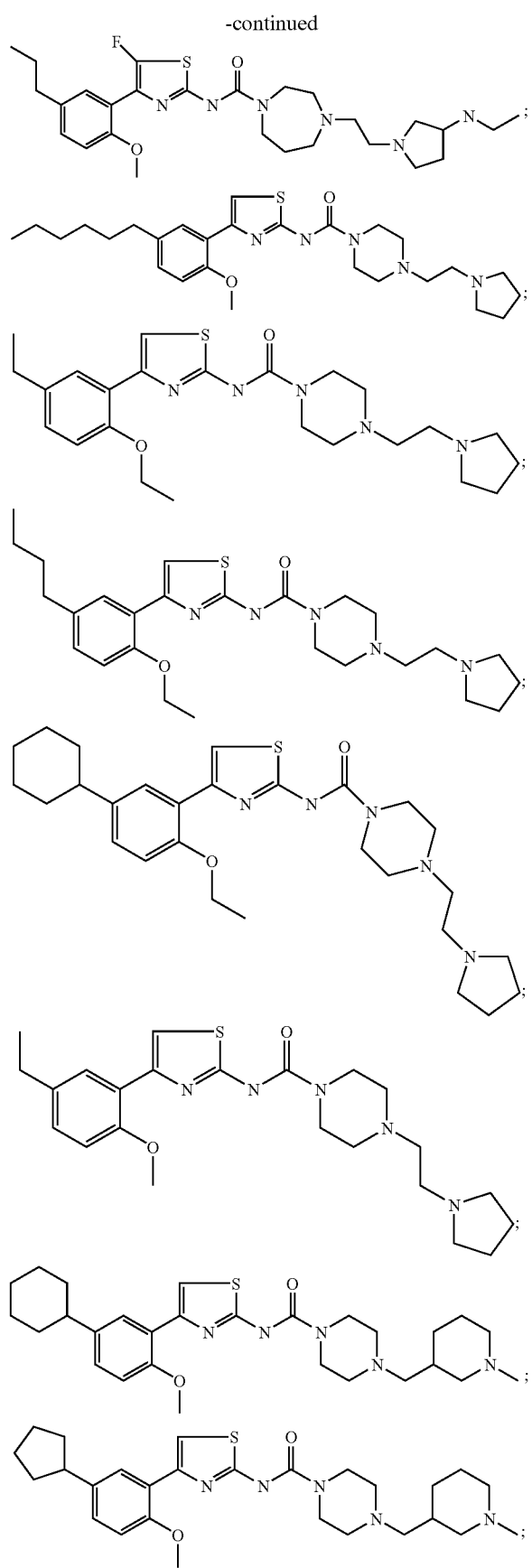
-continued
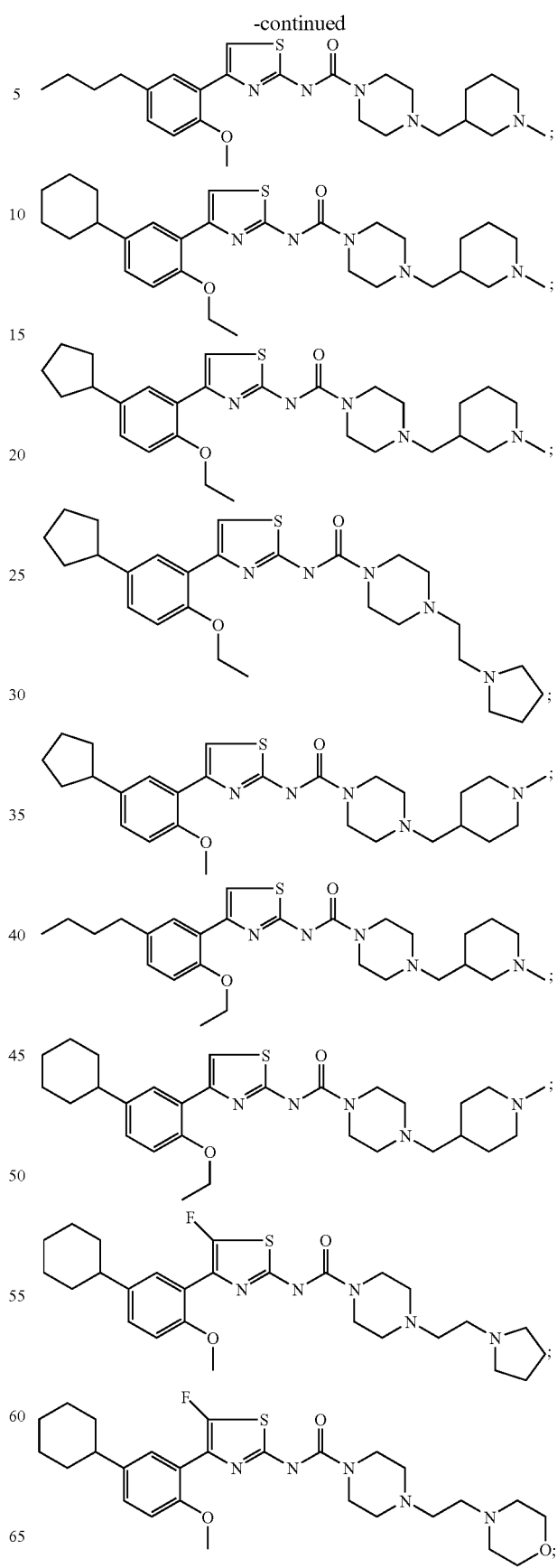

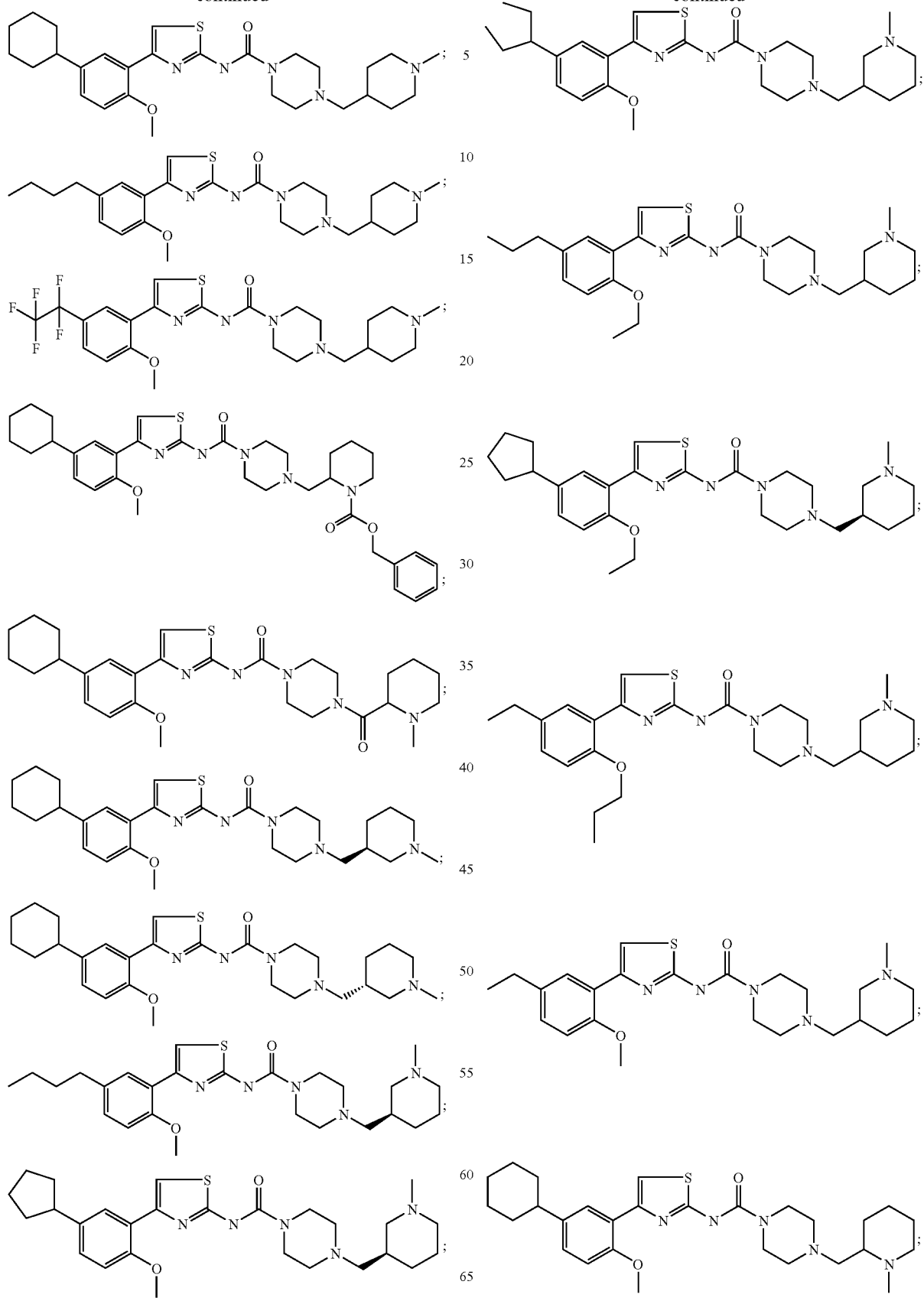

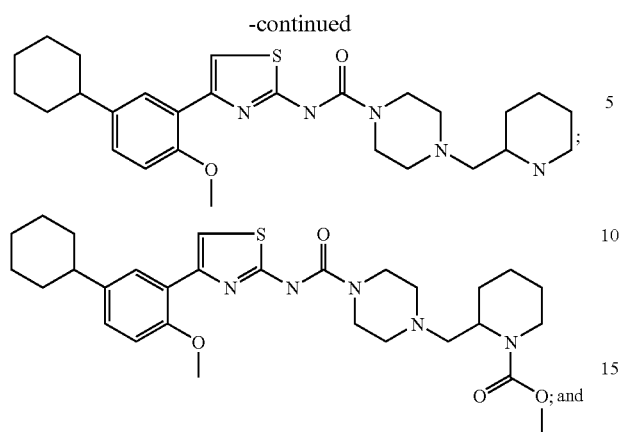
or a pharmaceutically acceptable salt thereof.
* * * * *

UNITED STATES PATENT AND TRADEMARK OFFICE
CERTIFICATE OF CORRECTION

PATENT NO. : 7,767,681 B2
APPLICATION NO. : 11/649316
DATED : August 3, 2010
INVENTOR(S) : Pierre Casellas et al.

It is certified that error appears in the above-identified patent and that said Letters Patent is hereby corrected as shown below:

On the first page, in field (57), in column 2, in "Abstract", line 6, delete " 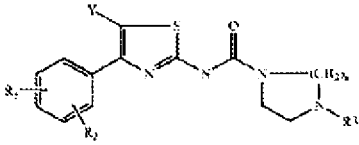 " and insert -- 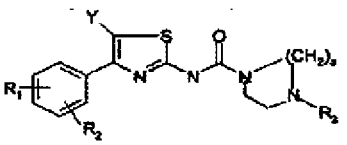 --, therefor.

In column 1, line 11-20, delete " 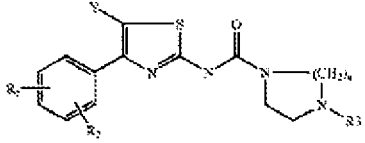 " and insert -- 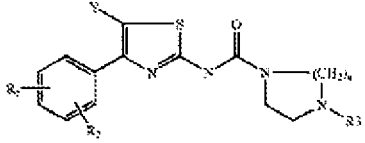 --, therefor.

In column 1, line 27, delete "—O-trifluoro ($C_1$-$C_8$)alkyl," and insert-- —O-trifluoro($C_1$-$C_8$)alkyl, --, therefor.

In column 7, line 12, delete "Y=H," and insert -- Y=H, --, therefor.

In column 7, line 42, delete "Y=H," and insert -- Y=H, --, therefor.

In column 7, line 43, delete "Y=F" and insert -- Y=F --, therefor.

In column 8, line 12, delete "$R'_2$=$R_2$=($C_1$-$C_4$)perfluoroalkyl;" and insert -- $R'_2$ = $R_2$ = ($C_1$-$C_4$)perfluoroalkyl; --, therefor.

Signed and Sealed this
Seventh Day of June, 2011

David J. Kappos
*Director of the United States Patent and Trademark Office*

In column 9, line 5-10, delete "  " and insert --  --, therefor.

In column 9, line 11, delete "($c_1$-$c_4$)" and insert -- ($C_1$-$C_4$) --, therefor.

In column 9, line 49, delete "($c_1$-$c_4$)" and insert -- ($C_1$-$C_4$) --, therefor.

In column 13, line 53, delete "(Z=OH)." and insert -- (Z=OH). --, therefor.

In column 14, line 5-18, delete " 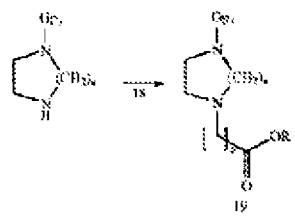 " and insert -- 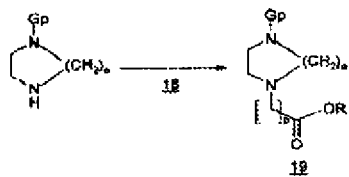 --, therefor.

In column 21, line 31, delete "Pentafluroethyl" and insert -- Pentafluoroethyl --, therefor.

In column 21, line 38, delete "Starck" and insert -- Stark --, therefor.

In column 24, line 33, delete "—" and insert -- HBr --, therefor.

In column 28, line 59, delete "LiA1H$_4$" and insert -- LiAlH$_4$ --, therefor.

In column 35-36, line 9, delete " 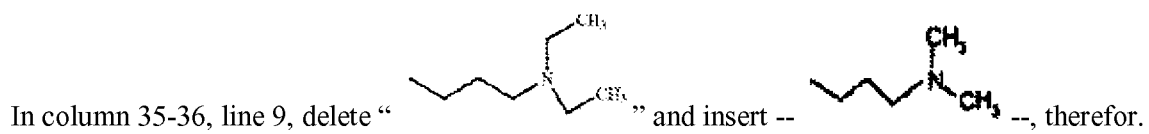 " and insert -- 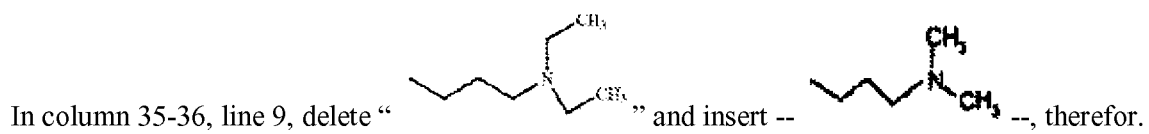 --, therefor.

In column 35-36, line 10, delete " 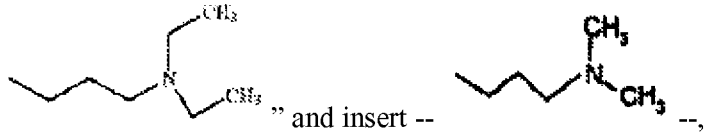 " and insert -- 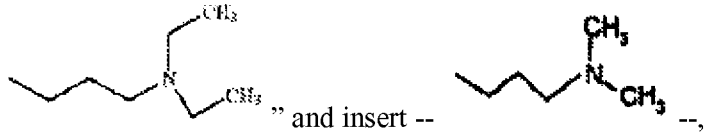 --, therefor.

In column 35-36, line 12, delete "180° C." and insert -- 245° C. --, therefor.

In column 37-38, line 7, delete "  " and insert --  --, therefor.

In column 37-38, line 8, delete "  " and insert --  --, therefor.

In column 37-38, line 9, delete "  " and insert --  --, therefor.

In column 37-38, line 11, delete "  " and insert --  --, therefor.

In column 37-38, line 12, delete "  " and insert --  --, therefor.

In column 39-40, line 6, delete "  " and insert --  --, therefor.

In column 39-40, line 8, delete "  " and insert --  --, therefor.

In column 43-44, line 11, delete "—oCH$_3$" and insert -- —OCH$_3$ --, therefor.

In column 45-46, line 4, delete " 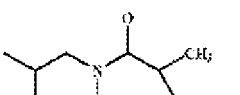 " and insert -- 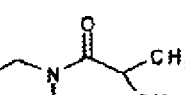 --, therefor.

In column 45-46, line 5, delete " 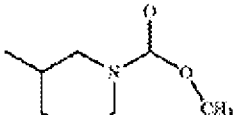 " and insert -- 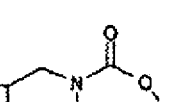 --, therefor.

In column 47-48, line 8, delete " 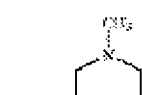 " and insert --  --, therefor.

In column 53-54, line 13, delete "a_D" and insert -- $\alpha_D$ --, therefor.

In column 55-56, line 4, below

" 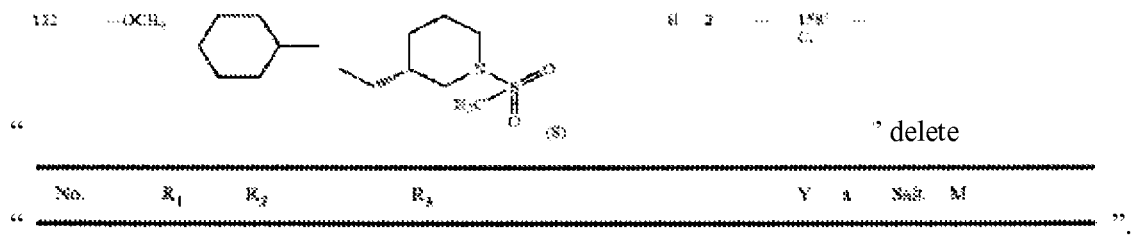 " delete

" 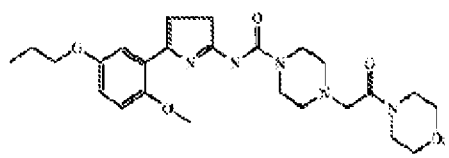 ".

In column 58, line 22, delete "hypersenstitivity," and insert -- hypersensitivity, --, therefor.

In column 58, line 47, delete "intamuscular," and insert -- intramuscular, --, therefor.

In column 59, line 5, delete "croscaramellose" and insert -- croscarmellose --, therefor.

In column 60, line 2, in claim 1, delete "—(CH$_2$)OH," and insert -- —(CH$_2$)$_n$OH, --, therefor.

In column 60, line 24, in claim 1, delete "hetero aryl," and insert -- heteroaryl, --, therefor.

In column 60, line 49, in claim 1, delete "—NR$_4$R$_5$" and insert -- —NR$_4$R$_5$, --, therefor.

In column 62, line 64, in claim 9, delete " 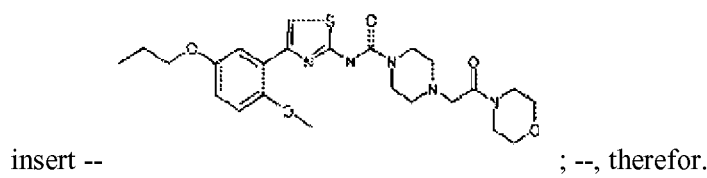 ;" and insert -- 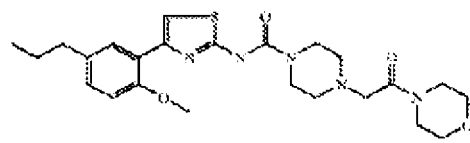 ; --, therefor.

In column 63, line 30-35, in claim 9, delete " ;" and insert -- 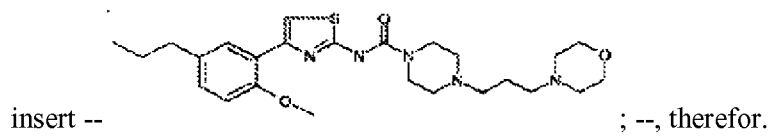 ; --, therefor.

CERTIFICATE OF CORRECTION (continued)
U.S. Pat. No. 7,767,681 B2

In column 63, line 65, in claim 9, delete " 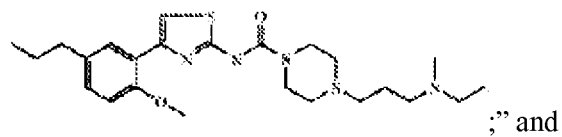 ;" and insert -- 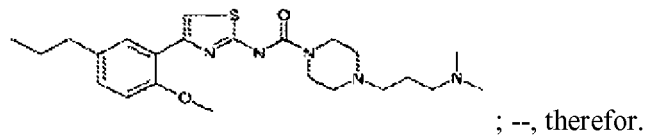 ; --, therefor.

In column 64, line 25-30, in claim 9, delete " 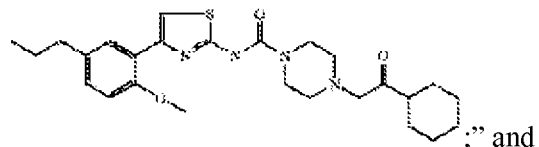 ;" and insert -- 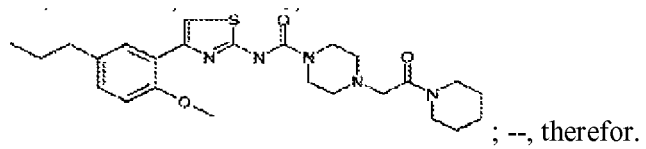 ; --, therefor.

In column 64, 30-45, in claim 9, delete " 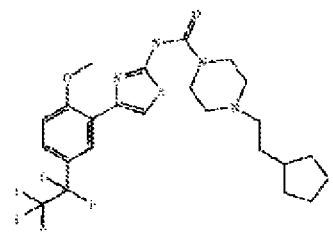 ;" and insert -- 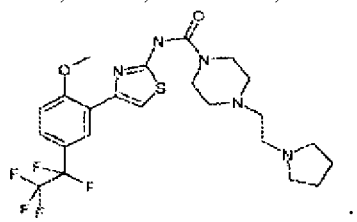 ; --, therefor.

In column 64, 45-55, in claim 9. delete " 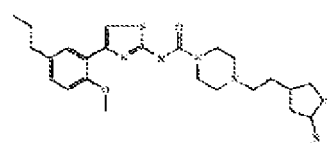 ;" and insert -- 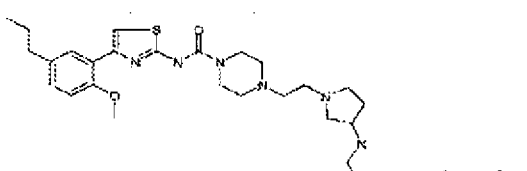 ; --, therefor.

In column 65, line 5, in claim 9, delete " 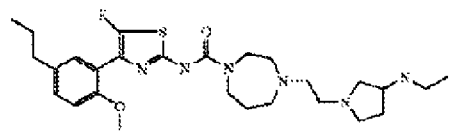 ;" and
insert -- 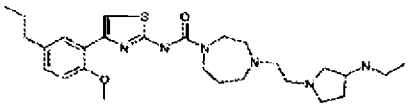 ; --, therefor.
In column 65, line 9, in claim 9, after " 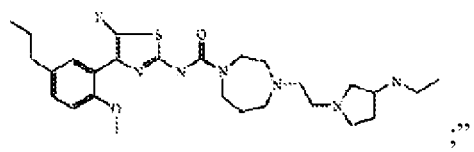 ;"
insert -- 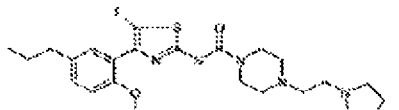 ; --.
In column 65, line 15-20, in claim 9, delete " 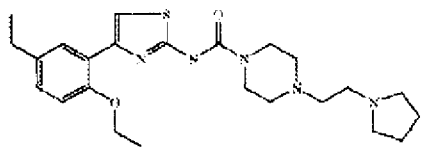 ;" and
insert -- 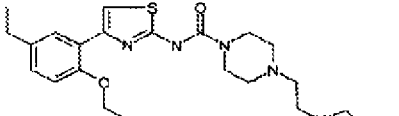 ; --, therefor.
In column 65, line 25-30, in claim 9, delete " 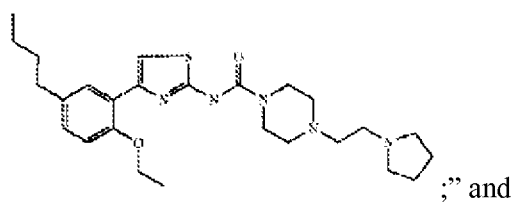 ;" and
insert -- 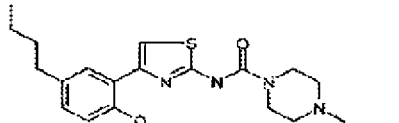 ; --, therefor.